(12) United States Patent
Chen

(10) Patent No.: US 11,041,843 B2
(45) Date of Patent: Jun. 22, 2021

(54) **ORGANIC TOROIDAL ARRAY APPARATUS OF MAKING FOR DIRECT AND REAGENT-FREE SENSING OF THE ENDOTOXIN ACTIVITIES OF A SINGLE *E. COLI* CELL**

(71) Applicant: Ellen Tuanying Chen, Rockville, MD (US)

(72) Inventor: Ellen Tuanying Chen, Rockville, MD (US)

( * ) Notice: Subject to any disclaimer, the term of this patent is extended or adjusted under 35 U.S.C. 154(b) by 119 days.

(21) Appl. No.: 15/984,349

(22) Filed: May 19, 2018

(65) Prior Publication Data

US 2019/0137477 A1    May 9, 2019

Related U.S. Application Data

(63) Continuation of application No. 15/602,103, filed on May 23, 2017, now abandoned.

(60) Provisional application No. 62/339,829, filed on May 21, 2016.

(51) Int. Cl.
*G01N 33/00* (2006.01)
*C12Q 1/00* (2006.01)
*G01N 33/487* (2006.01)
*G01N 27/416* (2006.01)

(52) U.S. Cl.
CPC ... *G01N 33/48714* (2013.01); *G01N 27/4161* (2013.01)

(58) Field of Classification Search
CPC .......................... G01N 33/48714; C12Q 1/002
See application file for complete search history.

(56) References Cited

U.S. PATENT DOCUMENTS

2012/0193243 A1 * 8/2012 Chen ................ G01N 33/57492
205/777.5

* cited by examiner

*Primary Examiner* — Nathan A Bowers

(57) ABSTRACT

The invented organic memristor/memcapacitor device comprises arrayed cross-bar donut-shape toroidal matrix self-assembling membrane on an electrode mimicking mitochondria's double membrane surface structure and the direct electron-relay function, that used to mimic functions of Fibroblast Growth Factor Receptor 1 (FGFR1) and choline acetyltransferase (CHAT), which enables bio-communication signals flowing directly between the endotoxin interacted membrane electrode assembly (MEA) working electrode and a cathodic electrode; and from a biomarker Acetyl coenzyme A (AcCoA) interacted the MEA electrode and the cathodic electrode when applied a definite potential, respectively, for detection of a single *E. coli* cell and detection of a picomolar concentration of AcCoA under nature enzyme-free, antibody-free and reagent-free conditions. The sensor offers multiple functions for monitoring neuronal synapse pulse energy output. The robust analytical performances of the device for monitoring endotoxins in milk are important in the dairy industry.

5 Claims, 25 Drawing Sheets

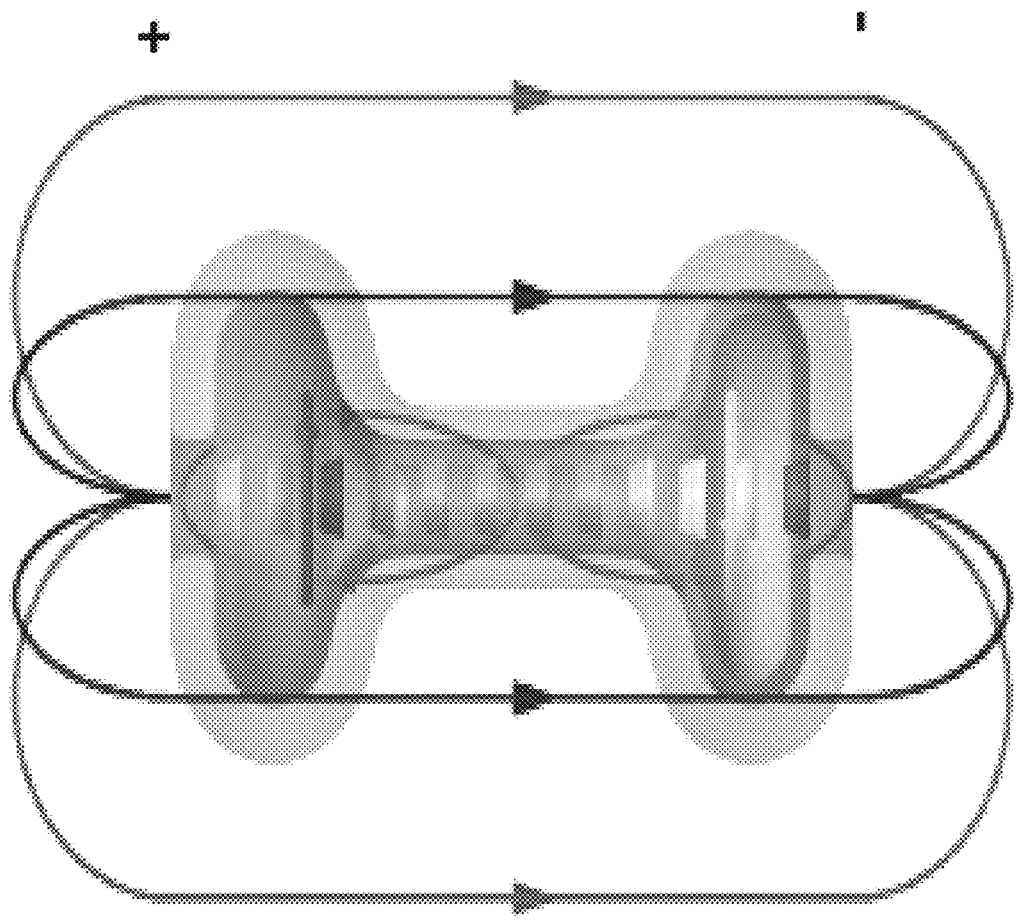

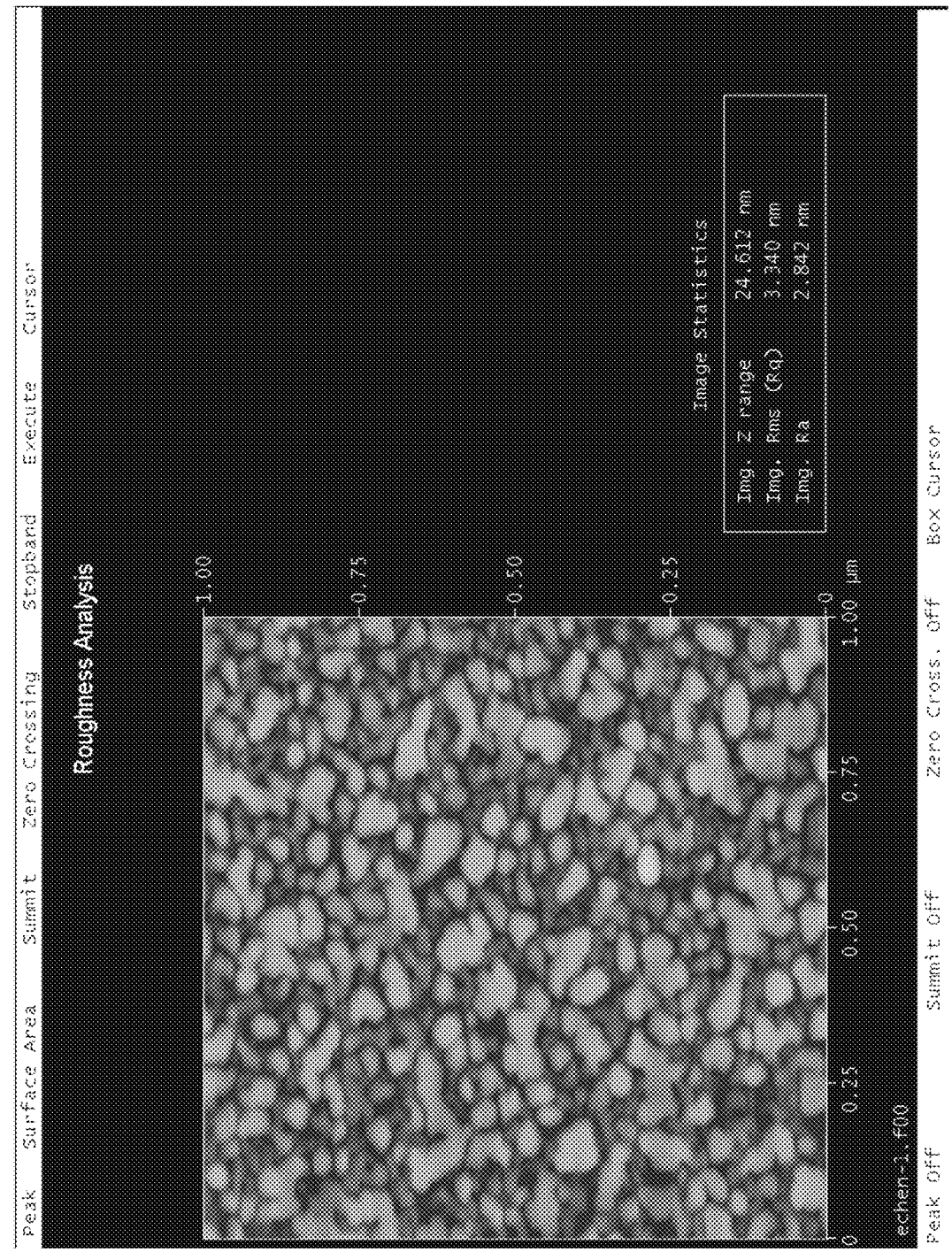

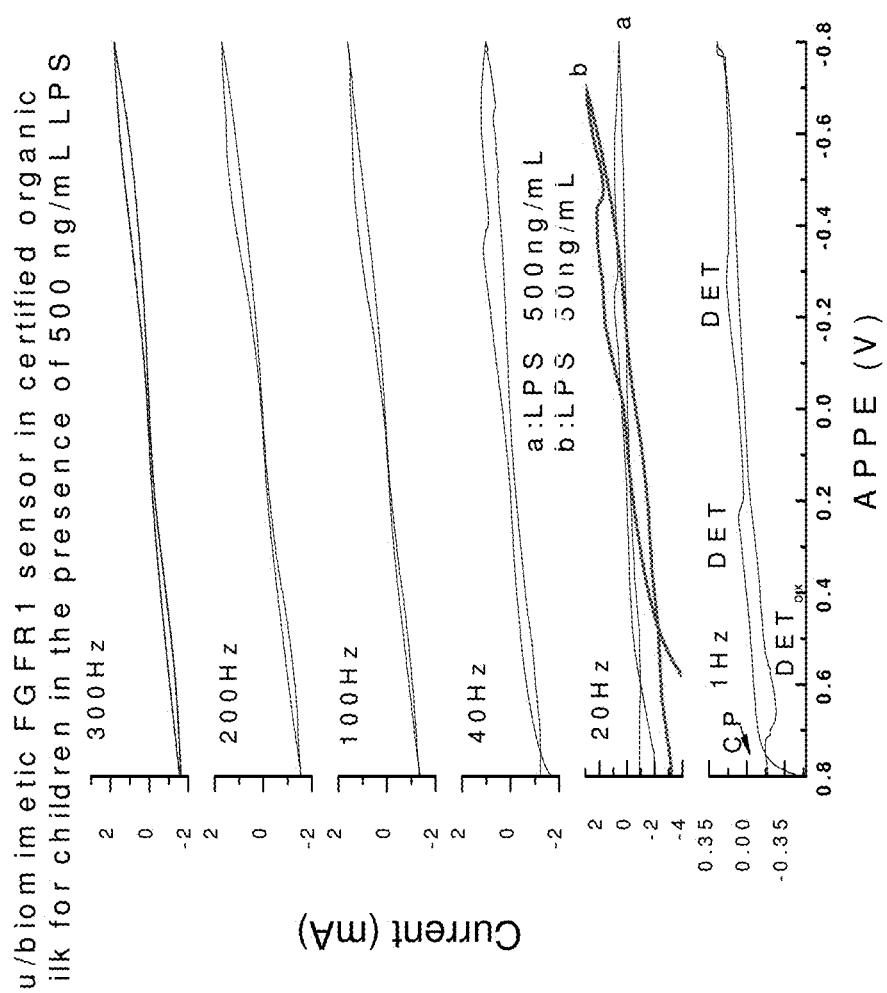

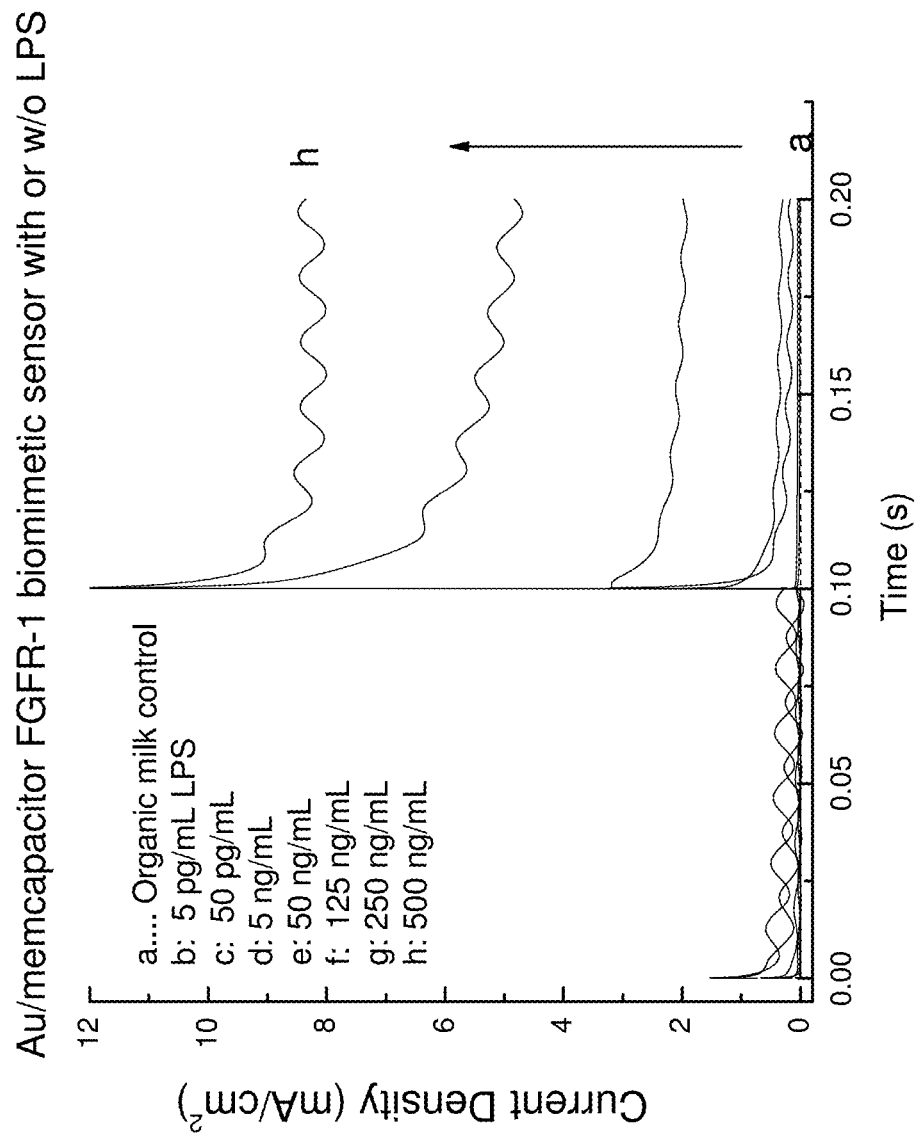

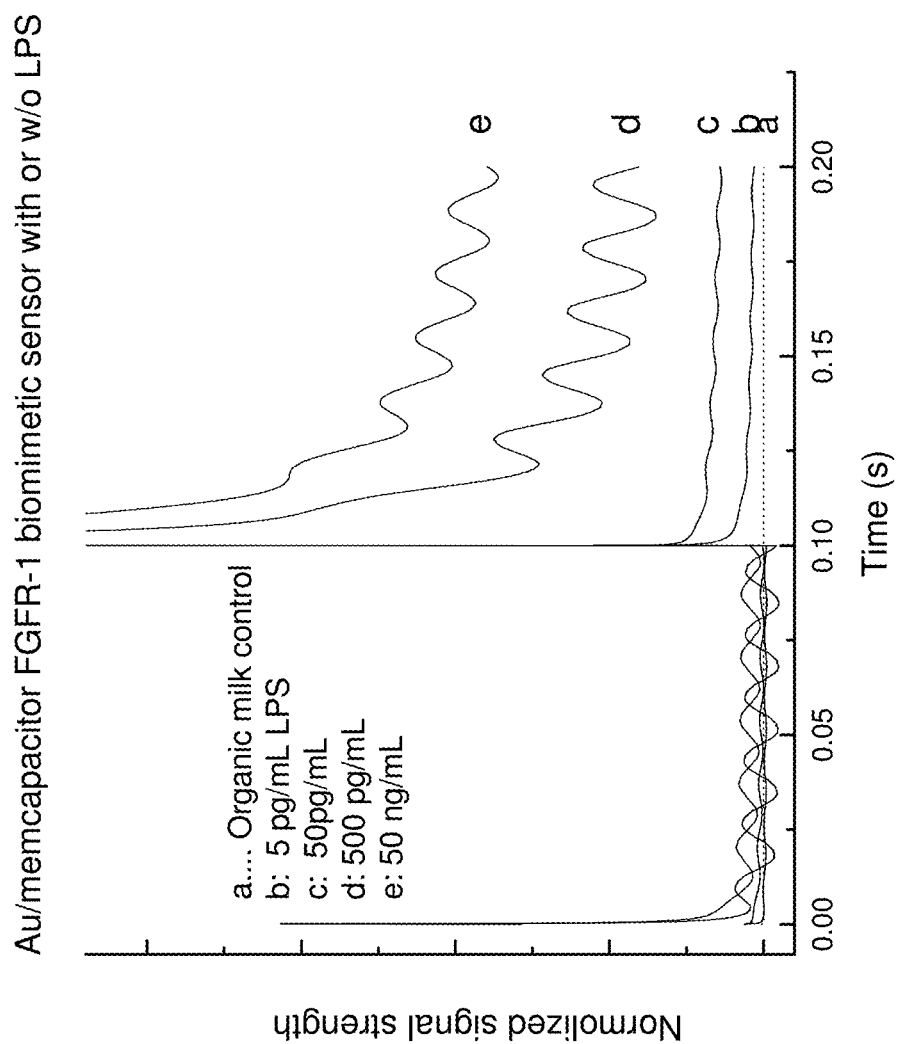

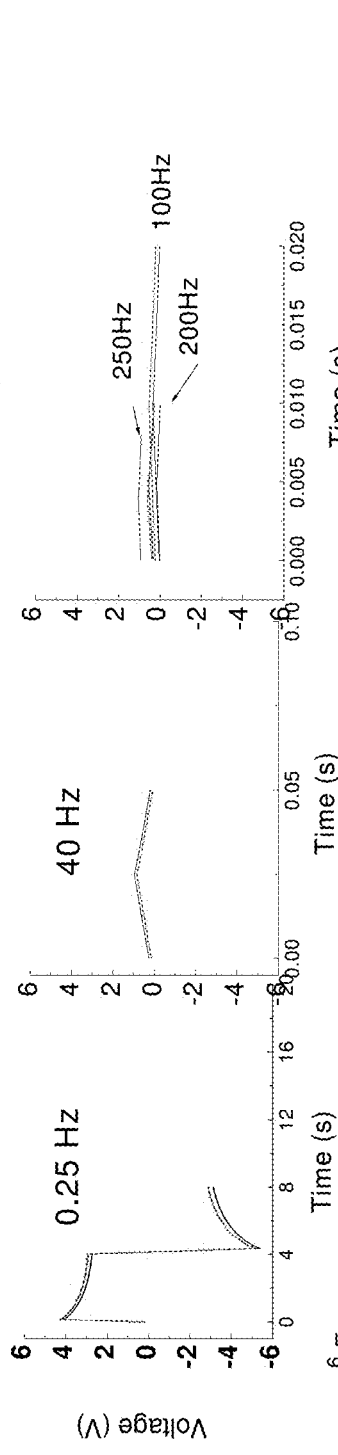

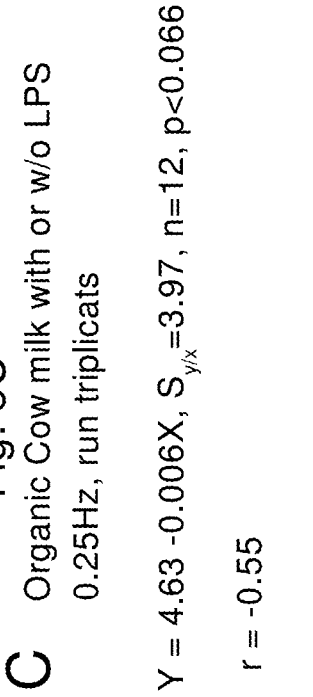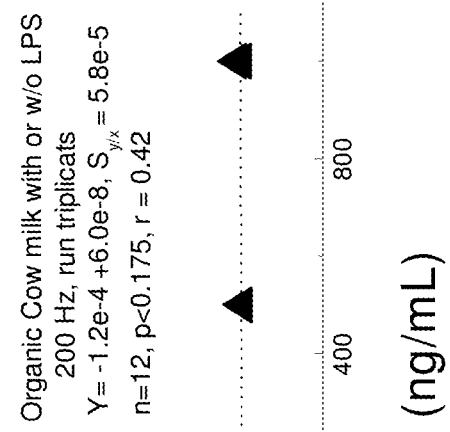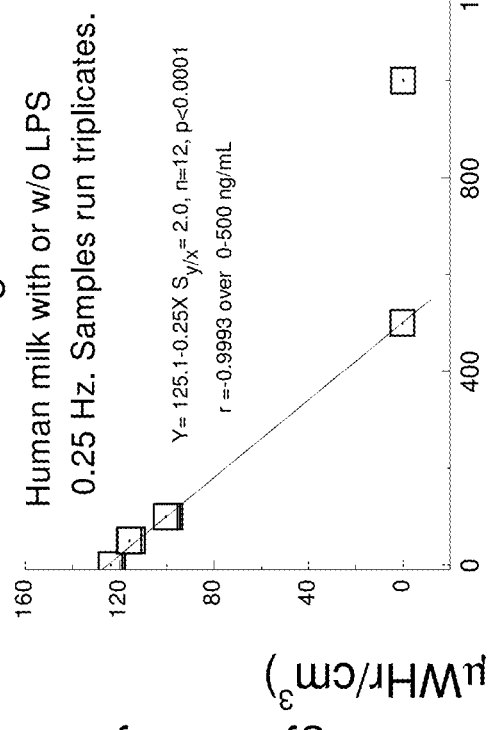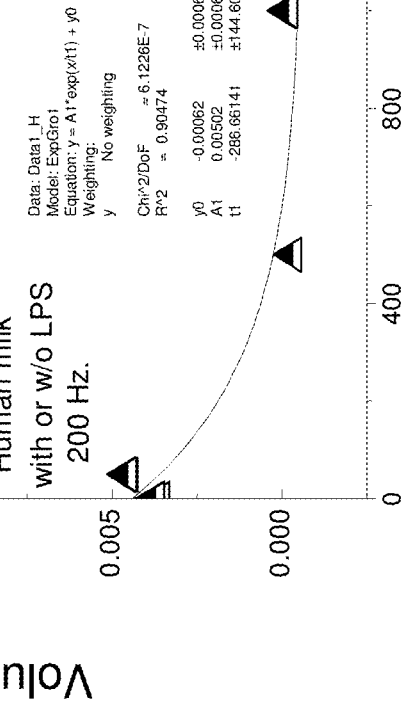

LPS concentration impacts on energy density Using the voltage sensing method

Fig. 8A — Human milk with or w/o LPS, 0.25 Hz. Samples run triplicates. Y = 125.1 − 0.25X, $S_{y/x}$ = 2.0, n=12, p<0.0001, r = −0.9993 over 0-500 ng/mL Fig. 8B — Human milk with or w/o LPS, 200 Hz.
Data: Data1_H
Model: ExpGro1
Equation: y = A1*exp(x/t1) + y0
Weighting: y No weighting
Chi^2/DoF = 6.1226E-7
R^2 = 0.90474
y0  −0.00062  ±0.00066
A1   0.00502  ±0.00067
t1  −286.66141 ±144.60689

Fig. 8C — Organic Cow milk with or w/o LPS, 0.25Hz, run triplicats. Y = 4.63 − 0.006X, $S_{y/x}$ = 3.97, n=12, p<0.066, r = −0.55

Fig. 8D — Organic Cow milk with or w/o LPS, 200 Hz, run triplicats. Y = −1.2e-4 + 6.0e-8, $S_{y/x}$ = 5.8e-5, n=12, p<0.175, r = 0.42

Volumetric Energy Density ($\mu$WHr/cm$^3$)

LPS Concentration (ng/mL)

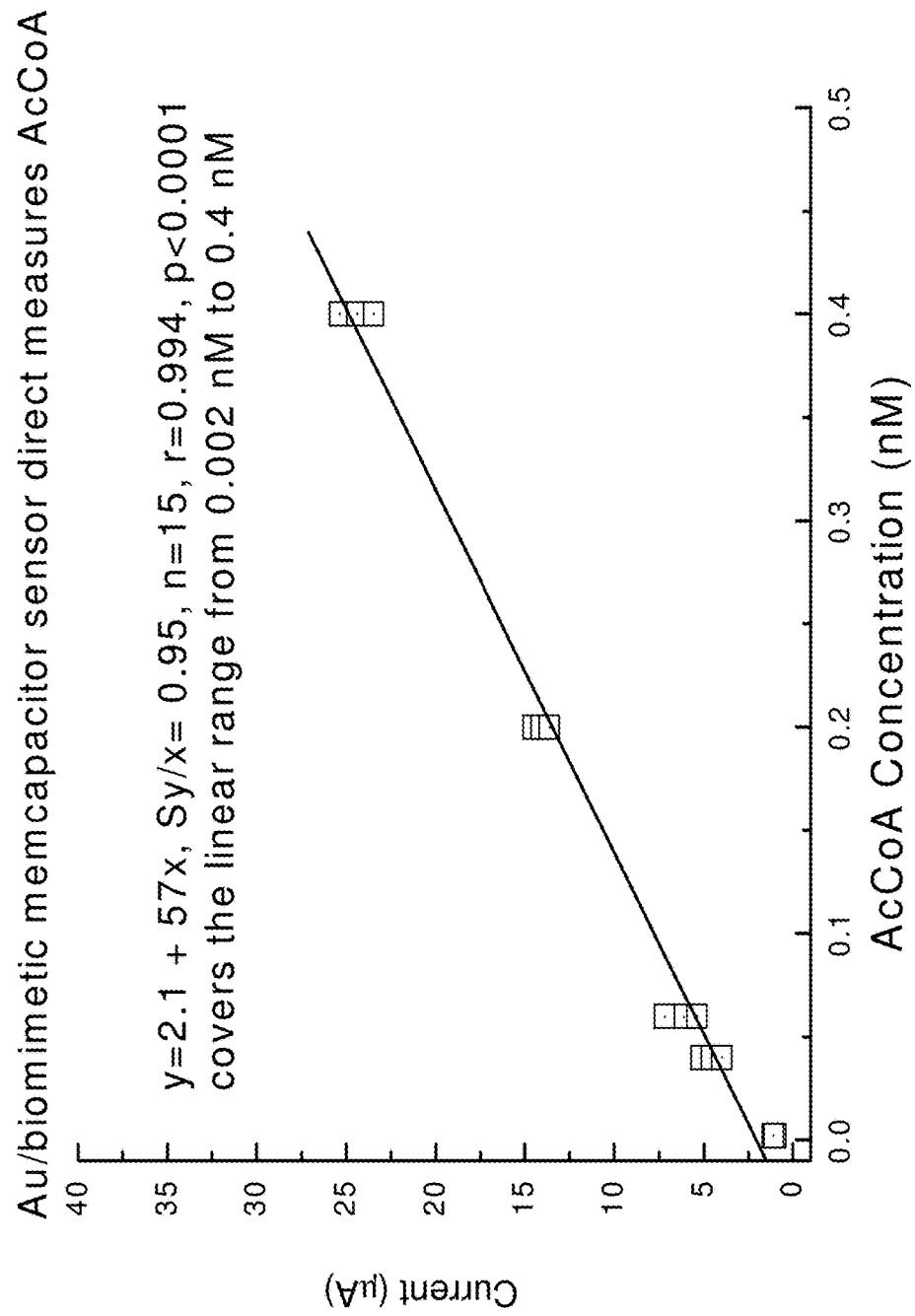

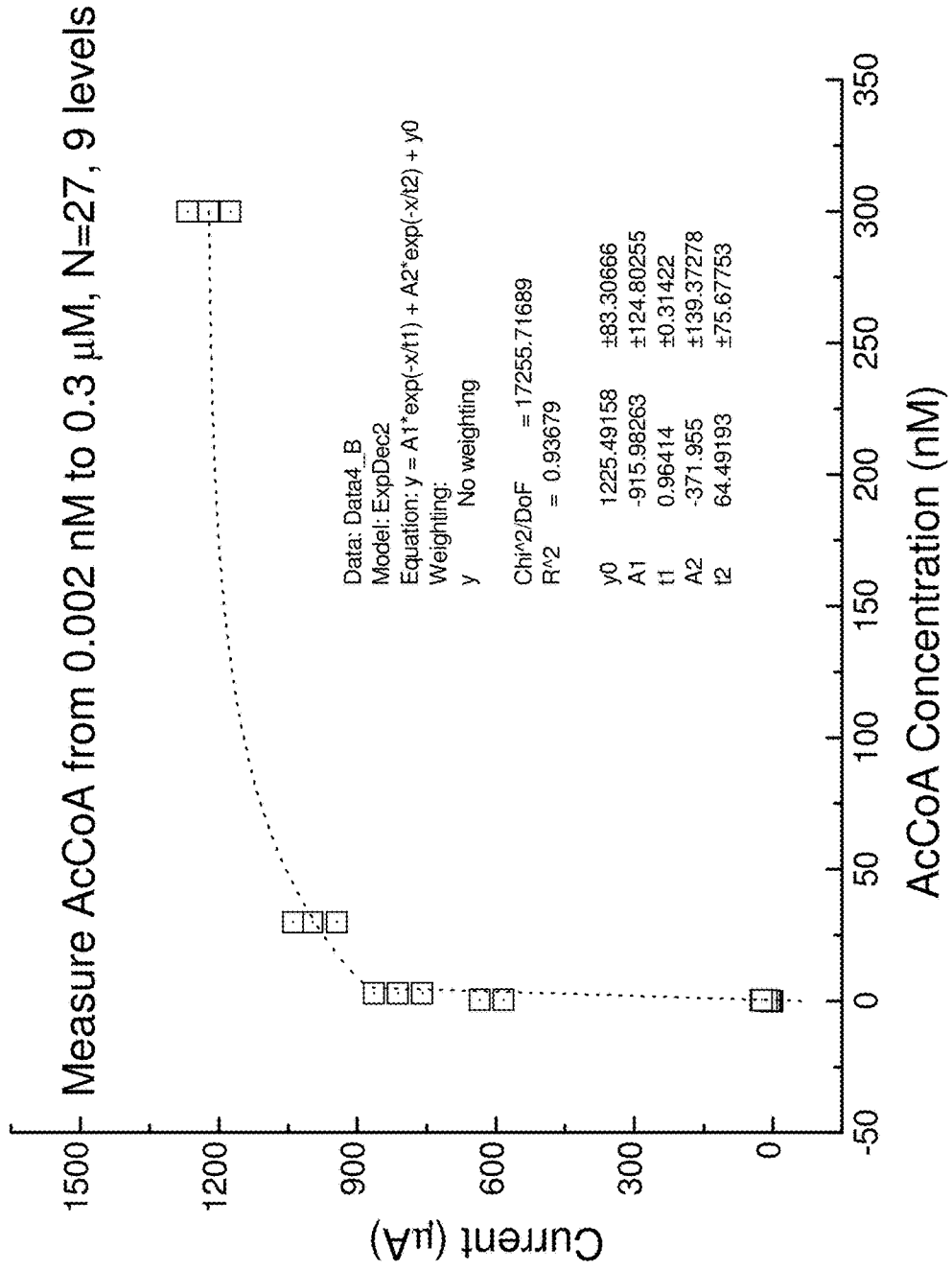

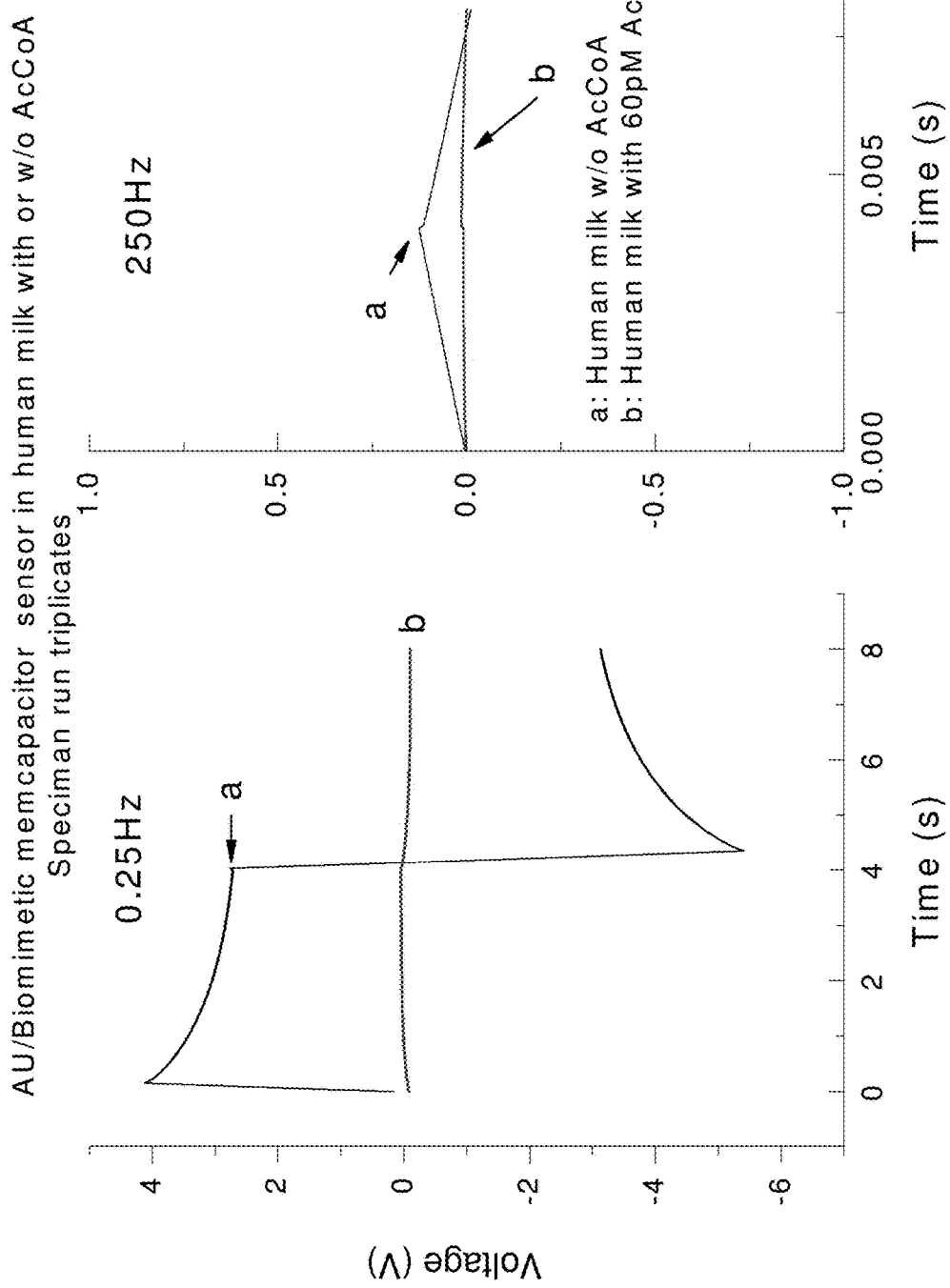

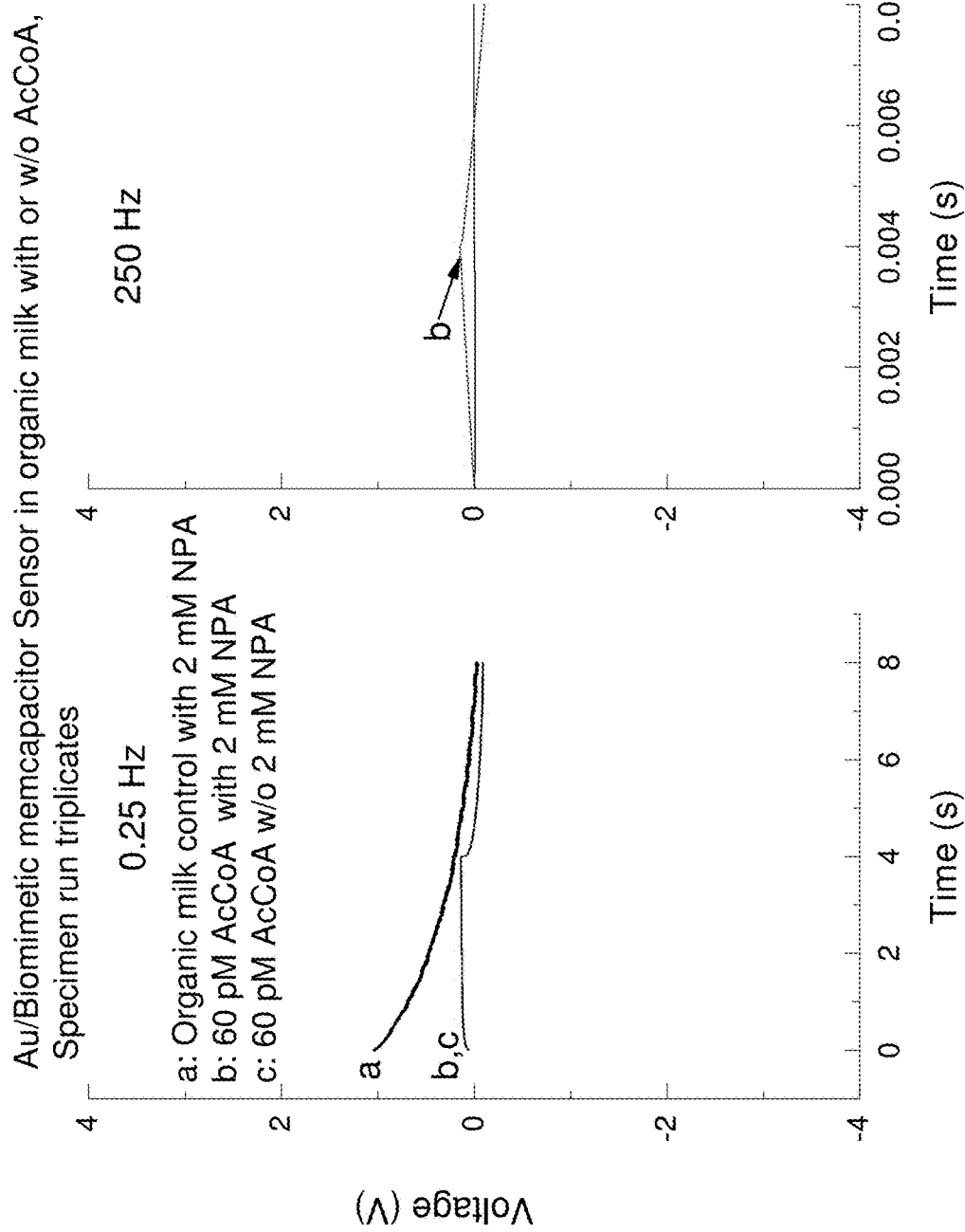

ORGANIC TOROIDAL ARRAY APPARATUS OF MAKING FOR DIRECT AND REAGENT-FREE SENSING OF THE ENDOTOXIN ACTIVITIES OF A SINGLE *E. COLI* CELL

CROSS-REFERENCE TO RELATED APPLICATIONS

This patent application claims the benefit of U.S. Provisional Patent Application Ser. No. 62/339,829 filed on May 21, 2016; U.S. non provisional application for extended missing parts pilot program Ser. No. 15/602,103, filed on May 23, 2017. The entire disclosure of the prior patent application Ser. No. 15/602,103 and 62/339,829 is hereby incorporated by references, as is set forth herein in its entirety.

FIELD OF THE INVENTION

The present invention relates to the field of electrochemical sensors, in particular, to a device having both characteristics in memristor/memcapacitor for direct sensing of endotoxin activities of single *E. coli* cell and other proteins in biological substances.

BACKGROUND OF THE INVENTION

Lipopolysaccharide (LPS) is a common endotoxin from *E. coli* bacteria, and is the major source causing infectious diseases over 20 million people worldwide. LPS is a major contaminant found in commercially available proteins, and it is also the major contaminate in biological ingredients in drugs and injectables, because even small amount of endotoxin can cause side effects such as endotoxic shock, injury, and even death; therefore, a strengthened standard of drug purity is needed. However, removing LPS from pharmaceutical products, for intravenous application to 5 endotoxin units (EU) per kg of body weight per hr, is a challenge to researchers who thought this standard is unachievable [1-2]. *E. coli* bacteria covers 75% its outer layer membrane with gram-negative endotoxin LPS, and it stimulates the host's immune response of cytokines [3-4]. Recently, researchers reported LPS penetrates the gut-immune-barrier (GIB) causing liver infection [5]; LPS leaking from the tight junction in the gut membrane into the blood stream cause many diseases, autism, obesity, diabetes, Alzheimer's, chronic pain, and inflammation [6-10]. Furthermore, LPS can break the blood-milk barrier into the milk and may cause harm, as reported from collected cow milk, which was compromised by LPS, and may have caused mastitis [11]. A recently published paper reported human milk offers an advantage to correlate positively with gut microbiota and to maintain healthy oligosaccharide (HMO) isomers which are specific to human milk and that are necessary in the newborn infant's gut in the first week [12].

A paramount challenge was put on the researchers and industry as a whole for improving the LPS detection methods with more simplified procedure, more accuracy and precision, faster, and more affordable options. Because previously, a lack of sensitivity associated with the protein interference plus time consuming antibody and tracer assays hampered the ability to realize the unmet goals and fulfill these needs.

It is a well-accepted fact that breast-feeding offers more benefits for human babies' growth in nutritional and immune defense over cow milk [13-15], and it has been strongly recommended, as published by the World Health Organization [15]. We found very few tests or sensors, if any, to assess the energy outcomes at different neuronal synapse frequencies, such as slow-wave-sleeping and fast gamma frequency, between breast-feeding using human milk as compared with feeding organic cow milk in the presence of LPS challenge. We believe that this testing is important because not only it will increase our knowledge, but also it will provide first hand convincing evidence for preferring human milk for feeding infants in regards to the energy requirement for mental and physical development of infants. Our goal for this project is to develop a nanostructured memcapacitor/memristor sensor for antibody-free, reagent-free direct measurement of pg LPS, and to assess the energy outcome comparing human milk with cow milk. The intention is that the memcapacitor/memristor device represents, in concept, a baby's single neuron to "feel" the energy gain or loss in the presence of LPS. This project is based on our prior experience in using the memristor/memcapacitor to mimic hippocampus-neocortex neuronal network circuitry [16-20].

Acetyl co-enzyme A (AcCoA) is a leading substrate in a large variety of enzyme-catalyzed reactions, such as for choline acetyltransferase (CHAT) and acetylcholinesterase (ACHE) [21-25]. Szutowicz's group emphasized that AcCoA is the key factor for the survival or death of cholinergic neurons in course of neurodegenerative diseases [25]. Ivan Gout's group emphasized that the level of AcCoA is crucial to early embryonic development [26]. AcCoA is a thioester derived from catabolism of all major carbon fuels. AcCoA may play a role in the energy production, metabolism, memory, cell proliferation and early childhood development, and it is central to biological acetylation reactions. AcCoA deficiency leads to many diseases, such as diabetes, cancer, coronary disease, autism, Alzheimer's, and sudden infant death syndrome. Abnormality of CHAT activity may lead to these diseases because CHAT represents the most specific cholinergic marker in the CNS [27-28] and the spatial temporal manifestation of CHAT has been examined at both the protein and mRNA levels in different tissues of various species [28].

Furthermore, reports revealed that the virus replications of West Nile virus (WNV), the neurotropic flavivirus that is transmitted by mosquito bites causing meningitis and encephalitis in humans [29], involved the carboxylation of AcCoA to malonyl CoA through AcCoA carboxylase [29]. Therefore, sensitive quantitation of the CHAT activity, in terms of monitoring the changes of substrate AcCoA in biological specimens, is on demand for monitoring and diagnosing various diseases.

Challenges exist for providing a non-enzymatic label-free, reagent-less detection device for the direct detection of AcCoA with rapid detection time, free specimen preparation, and pM high sensitivity are paramount in order to avoid time-consuming assays and protein interferences. Many native enzymatic methods reported to detect AcCoA have the concentration range between mM to µM, such as the CoA cycling method [23], the carbon radioactive tracer labeling method [30-31], and the gas chromatography-mass spectrometry method [32]. The HPLC antibody method can reach to 0.1 µM level of AcCoA [26]. In view of the drawbacks of these methods, none of these methods can provide adequate sensitivity in pM level and the short testing time needed for testing AcCoA inside of the mitochondria cell when newborns consume human milk compared with that of cow milk in order to monitor the quality of the milk for babies.

It is well accepted that breast-feeding offers more benefits for human babies' growth in nutritional content and immune defense support over that of cow milk consumption [13-15] and it is a strong recommendation published by the World Health Organization [15]. However, to actively pursue real-time monitoring of breastfeeding and obtain the preliminary data using an innovative device is not practically feasible now. The goal of this project is to develop a nanostructured memcapacitor/memristor sensor for antibody-free, reagent-less direct measure pM AcCoA at different frequencies to assess the energy outcome comparing human milk with cow milk without protein interference and in a real-time and sensitive manner. The memcapacitor/memristor device will represent, in concept, a human infant single brain neuron's ability to "feel" or sense the energy gain or loss that is due to the presence of AcCoA signaling with the biomimetic CHAT of the sensor membrane in a biological specimen. This project is based on our prior experience in memristor/memcapacitor to mimic hippocampus-neocortex neuronal network circuitry [16-20].

SUMMARY OF INVENTION

It is an object of the present invention to evaluate the immunological advantage of human milk vs. organic cow milk regarding the pHFO formation at LPS challenges.

The intention is that the memcapacitor/memristor device is a sensor that represents, in concept, a baby's single neuron which is able to "feel" and react to the energy gain or loss in the presence of LPS. Our focus will be to determine how the pHFO occurs with dosage changes of LPS and the frequency change from SWS to 200 Hz.

It is an object of the present invention to demonstrate the memristor/memcapacitor's immunological capability in a contour mapping, that is based on a dual quantitative measurement of LPS in amperometric/voltage method while showing the advantage of human milk over cow milk.

It is an object of the present invention to provide a new generation of organic memristor/memcapacitor having mitochondrion-like surface structure enables Biomimetic FGFR-1 function and in Biomimetic of CHAT function in direct electron-relay systems.

It is an object of the present invention to provide a new generation of organic memristor/memcapacitor that is capable for dual sensing of functioning of AcCoA and LPS in single cell using milk specimen in current and voltage change without using antibody, mediator, labels and tracers.

BRIEF DESCRIPTION OF THE DRAWINGS

FIG. 1 illustrates an art model for the 3D toroidal memcapacitor.

FIG. 2B depicts the 2D AFM of the nanostructured islands membrane on a 50 nm gold chip of above membrane.

In FIG. 4D, at 20 Hz, "a" curve depicts the milk sample spiked with a final concentration 50 ng/mL LPS in red; "b" curve depicts the control human milk sample; "c" curve depicts 500 ng/mL LPS spiked in the human milk sample in black.

FIG. 4E depicts the CV profiles in 500 ng/mL LPS in organic milk on the hysteresis of the i-V curves over 1 to 300 Hz. At 20 Hz, "a" curve depicts the milk sample spiked with a final concentration 500.0 ng/mL LPS in black; "b" curve depicts 50.0 ng/mL LPS spiked in the organic milk sample in red.

FIG. 5A depicts the CA curve profiles in organic milk samples with spiked LPS covered concentration from "a" to "h" with LPS at 0.0, 5.0 pg/mL, 50.0 pg/mL, 5.0 ng/mL, 50.0 ng/mL, 125.0 ng/mL, 250.0 ng/mL and 500 ng/mL. Each sample run triplicates.

FIG. 5B illustrates the CA profiles in organic milk samples with spiked LPS covered concentration from "a" to "e" with LPS at 0.0, 5.0 pg/mL, 50.0 pg/mL, 500.0 pg/mL, 50.0 ng/mL clearly showing at lower concentration range of LPS, the peak intensity is distinguishable between samples with LPS and the control. Each sample run triplicates.

FIG. 7A depicts two different media solutions affecting on the single neuronal pulses profiles at 0.25 Hz; FIG. 7B depicts the voltage profiles in 40 Hz and FIG. 7C depicts the profiles in 250 Hz between pH 7.0 PBS buffer (red curve) and the human milk without LPS (black curve), respectively at ±10 nA, each sample run triplicates. FIG. 7D depicts the DSCPO profiles with or without LPS over LPS concentration ranges at 0.0 (a), 50 (b), 100 (c), 500 (d) and 1000 ng/mL (e) at 0.25 Hz at ±10 nA with each sample run triplicates. Insert is the curves for LPS at 500 and 1000 ng/mL, respectively. FIG. 7E depicts the DSCPO profiles with or without LPS over LPS concentration ranges at 50 ng/mL (a), 500 ng/mL (b), 1,000 ng/mL (c) and 0.0 ng/mL as the control (d) at 200 Hz, respectively, each sample run triplicates.

FIG. 8A depicts the quantitative calibration plot of LPS in human milk at 0.25 Hz and FIG. 8B depicts the plot at 200 Hz compared with LPS in organic milk at 0.25 Hz (FIG. 8C) and 200 Hz in FIG. 8D.

FIG. 15 shows the calibration plot of current vs. AcCoA concentrations.

FIG. 16 depicts the extended plot of current vs. AcCoA concentrations from 2.0 pM up to 0.3 µM.

FIG. 17A depicts the voltage profiles of detections of spiked AcCoA in human milk compared with control at 0.25 Hz. FIG. 17B depicts the voltage profiles at 250 Hz.

FIG. 18A depicts voltage profiles of detections of spiked AcCoA in organic milk compared with control at 0.25 Hz. FIG. 18B depicts the voltage profiles of detections of spiked AcCoA in organic milk at 250 Hz.

DETAILED DESCRIPTION OF THE INVENTION

Example 1—Fabrication of the Nanostructure Self-Assembling Membrane (SAM) Gold Memristive/Memcapacitive Chips The nanostructured biomimetic SAM was freshly prepared according to the published procedures based on cross linked conductive polymers of triacetyl-ß-cyclodextrin (TCD), polyethylene glycol diglycidyl ether (PEG), poly(4-vinylpyridine) (PVP) and ß-CD copolymer with appropriate amount of propositions on gold chip [21-22]. The chemicals were purchased from Sigma and went through purification procedures before use. A mixture of o-nitrophenyl acetate (o-NPA) in a molar ratio 1000:1 to the TCD mixture was incubated for 2 hrs at 35° C.; then the mixture was injected onto the gold surface and incubated for 48 hrs at 35° C. After that, we followed the clean procedures for completion of the SAM fabrication [21-22]. The configuration of the memristive/memcapacitive device comprises a gold membrane electrode assembly (MEA) working electrode, as anode, and a bare gold electrode as cathode, having another bare gold electrode as the reference electrode. The three gold electrodes are configured on a flat nonconductive plastic substrate. The anode electrode diameter is 2 mm.

Example 2—Characterization of the Membrane

Figure 2A:
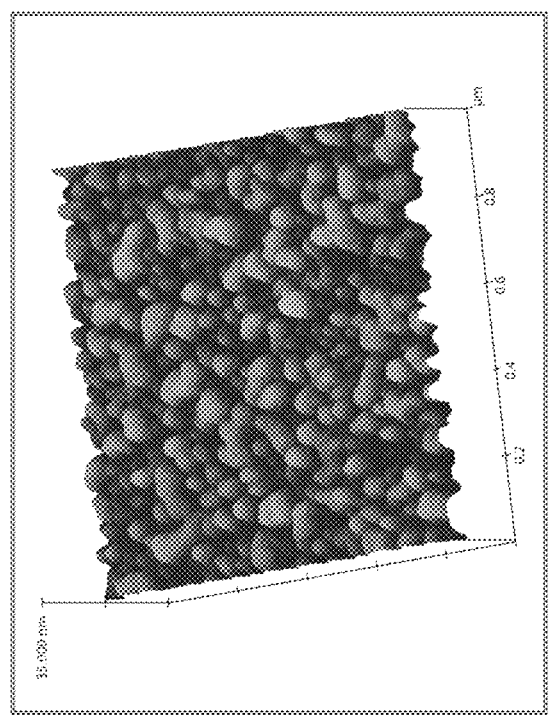
FIG. 2A depicts the 3D AFM image of the nanostructured islands membrane on a 50 nm gold chip of TCD/PEG/PVP and β-CD copolymer without o-NPA.

The morphology of the AU/SAM was characterized using an Atomic Force icroscope (AFM) (model Multimode 8 ScanAsyst, Bruker, Pa.). Data Collected in PeakForce Tapping Mode. Probes used were ScanAsyst-air probes (Bruker, Pa.). The silicon tips on silicon nitride cantilevers have 2-5 nm radius. The nominal spring constant 0.4 N/m was used. FIG. 1 illustrates an art model for the 3D toroidal memcapacitor. FIG. 2A depicts the 3D AFM image of horizontal conformational structure of the memristor/memcapacitor before the o-NPA was embedded on gold. FIG. 2B shows the 2D AFM image.

Example 3—Advantage of AcCoA's Rate Limiting Binding

Figure 3A:
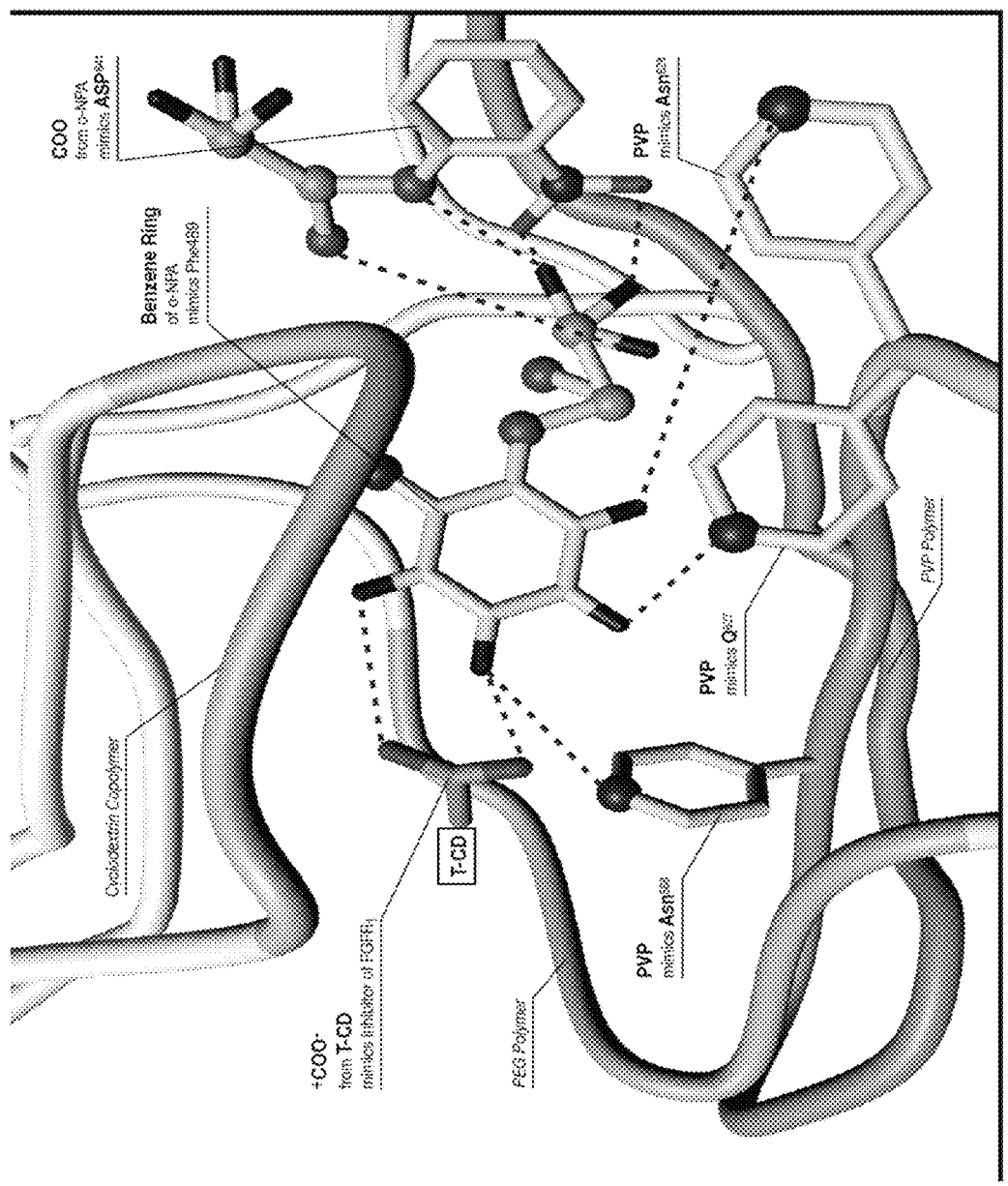
FIG. 3A depicts the art model of the SAM molecular polymer architecture for mimicking FGFR-1 in the presence of o-NPA.
Figure 3B:
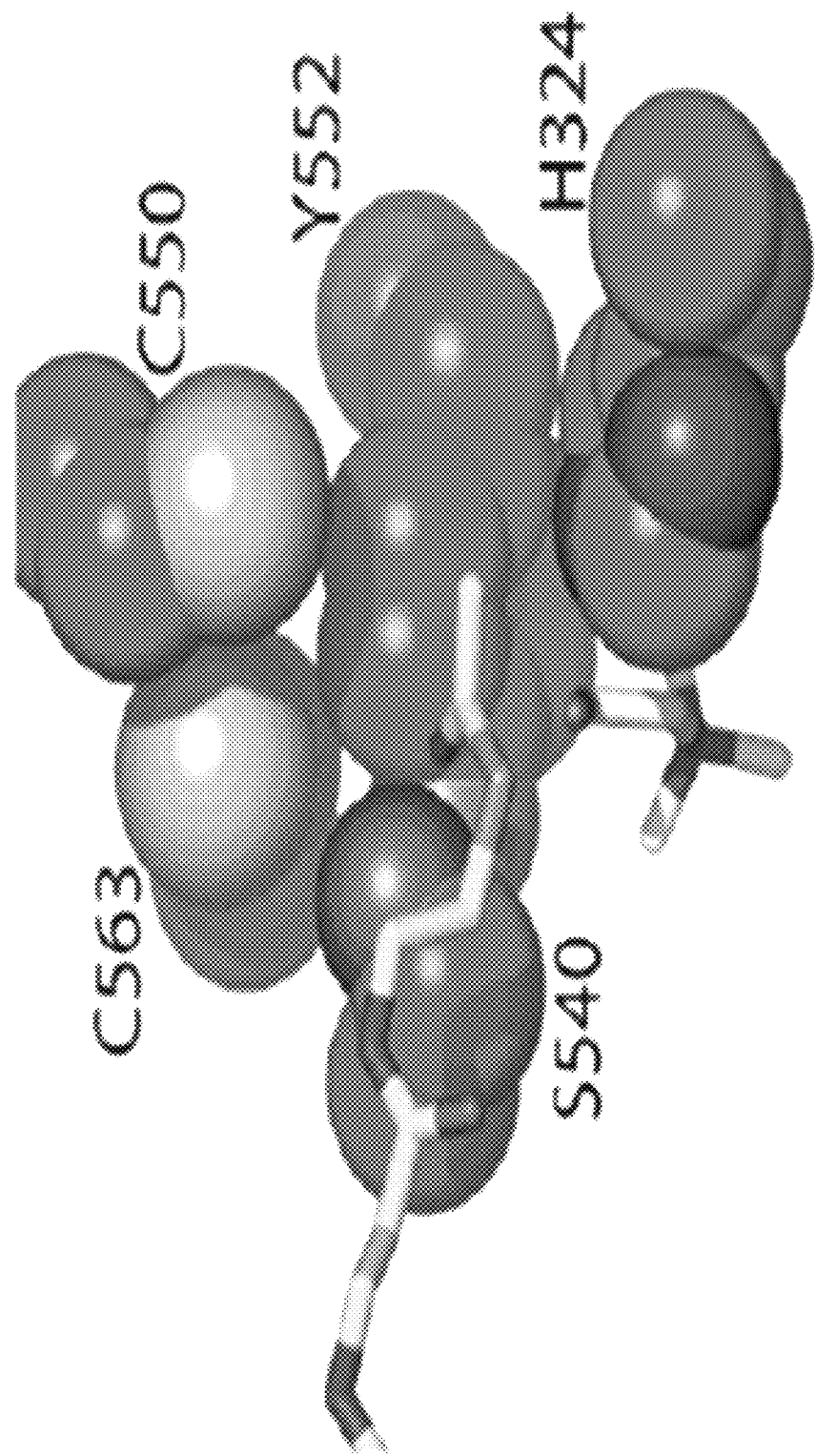
FIG. 3B depicts the art model of the SAM molecular polymer architecture for mimicking active sits of CHAT.

Using the nano island structure SAM to mimic the function of Fibroblast Growth Factors Receptor-1 (FGFR-1) for improving fuel cell function was reported as shown in FIG. 3A [E. Chen's U.S. Pat. No. 8,632,925, Jan. 21, 2014]. It plays important roles in embryonic development, angiogenesis, wound healing, and malignant transformation (11). We thought using the function groups in the SAM membrane to mimic the AcCoA's human choline acetyletransferase (CHAT) binding sites intrinsically to mitochondria's double membrane compartment with the structure needed may be a simplified approach as a neuronal sensor model. The model of the device is to mimic CHAT's function in emphasizing of AcCoA's rate limiting step binding [1-5]. The possible electron-relay was proposed by the pyridine group in PVP, the $COO^-$ group of TCD, the OH group from β-CD copolymer, and the carbonyl group from o-NPA through hydrogen bindings to be able to mimic s540, y552, c563, c550 and h324 of AcCoA binding sits in CHAT as Shown in FIG. 3B. The innovative approach is to first direct detect AcCoA in the mimicking binding sites of CHAT, without choline participates in the direct detection of AcCoA.

Figure 3C:
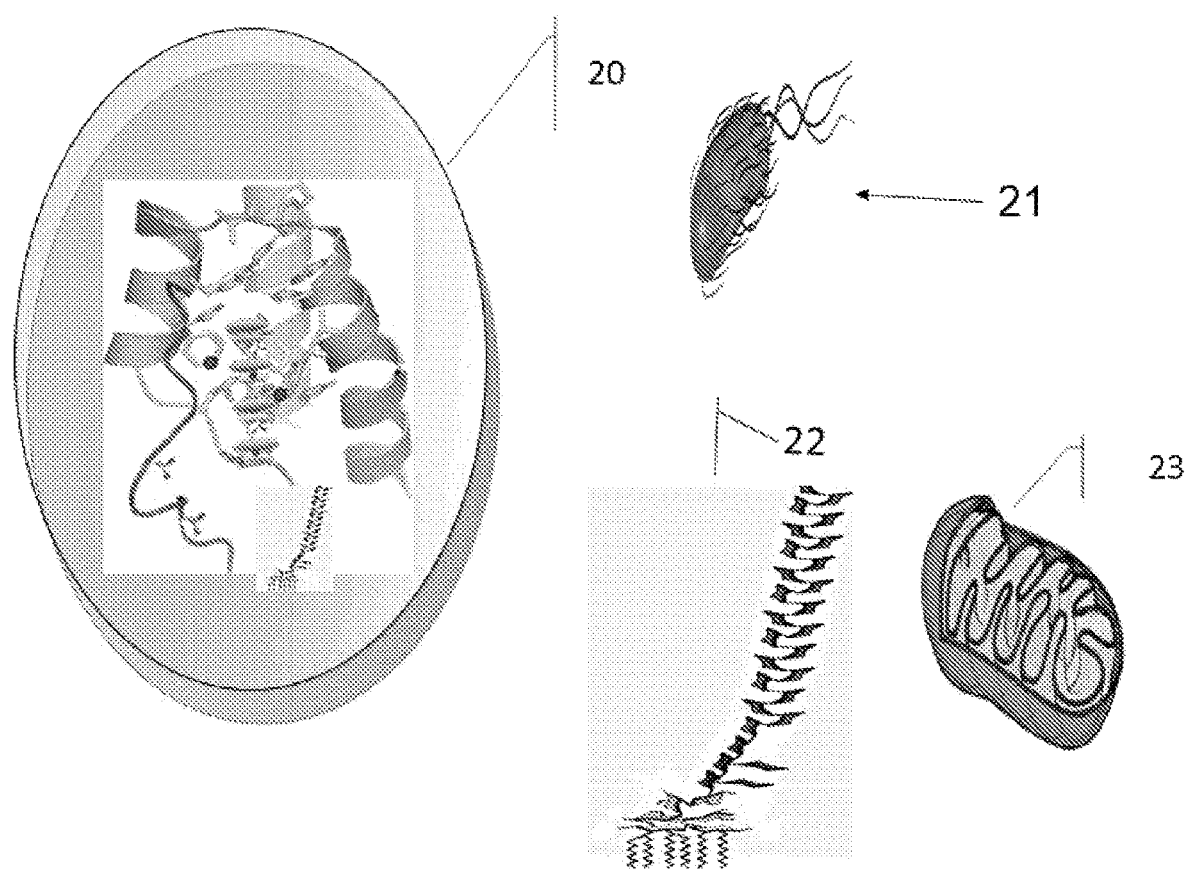
FIG. 3C depicts an art model of biomimetic FGFR1 of tyrosine kinase mitochondria-like double layer membrane SAM on an electrode by cross-linked with TCD, PEG, PVP and beta-cyclodextrin (beta-CD) copolymers with embedded o-NPA forms a toroidal array that interacts with an amphiphilic O antigen on the outer membrane of $E$ $coli$ O157:H7 as shown "20"; "21" refers to the LPS located on the outer membrane of the $E$ $coli$ cell; "22" refers to the structure of LPS comprises of O antigen, outer core oligo-saccharide, inner core and lipid A. "23" refers to a art model of mitochondria cell comprises of outer layer membrane, inner membrane, intermembrane space, matrix, DNA and cristae.

Example 4—Biomimetic Fibroblast Growth Factor Receptor 1 (FGFR1) SAM Membrane FGFR1 is one of family receptors of tyrosine kinases. It plays important roles in embryonic development, angiogenesis, wound healing, and malignant transformation, bone development, and metabolism [35-36]. Y. Zhang's group reported mice with deleted FGFR1 exhibited an increased mobilization of endothelial progenitor cells (EPCs) into peripheral blood undergoing endotoximia, and the endotoximia was induced by injection of LPS [36]. Our project's initial step is to build a model device such that the device's SAM membrane mimics the FGFR1 receptor in the presence of LPS, which acts as a model metabolic product to access the FGFR1 function. By using this model to compare the effects of fresh human milk and organic cow milk at different frequencies of neuronal action/resting pulses at SWS and fast gamma frequency with or without LPS conditions to find out whether or not milk samples are energy efficiency or deficiency on the biomimetic brain cells will provide useful information to reveal which type of milk samples is immunologically advantage to infants. FIG. 3A shows the electron-relay system, and FIGS. 2A and 2B are the AFM images in 3D and 2D on a gold chip with the TCD/PEG/PVP/copolymer before adding o-NPA for embedding. FIG. 3C depicts an art model of biomimetic FGFR1 of tyrosine kinase mitochondrion-like double layer membrane SAM on an electrode by cross-linked with TCD, PEG, PVP and beta-cyclodextrin (beta-CD) copolymers with embedded o-NPA forms a toroidal array that interacts with an amphiphilic O antigen on the outer membrane of E coli O157:H7 as shown "20"; "21" refers to the LPS located on the outer membrane of the E coli cell; "22" refers to the structure of LPS comprises of O antigen, outer core oligosaccharide, inner core and lipid A. "23" refers to a art model of mitochondria cell comprises of outer layer membrane, inner membrane, intermembrane space, matrix, DNA and cristae.

Example 5—Frequency Affects on Memristor/Memcapacitor's Performance

Evaluations of frequency's affect on memristor performance were conducted by Cyclic Voltammetric method (CV) in pH 7.0 saline solution at room temperature from a scan rate of 1 Hz to 1 KHz without using any biological specimen. Data are to be used for comparison between fresh human milk and USDA certified organic milk for infants with or without the presence of LPS covering the same range of real-time synapse action/resting potential pulses at different frequencies against controls.

Figure 4A:
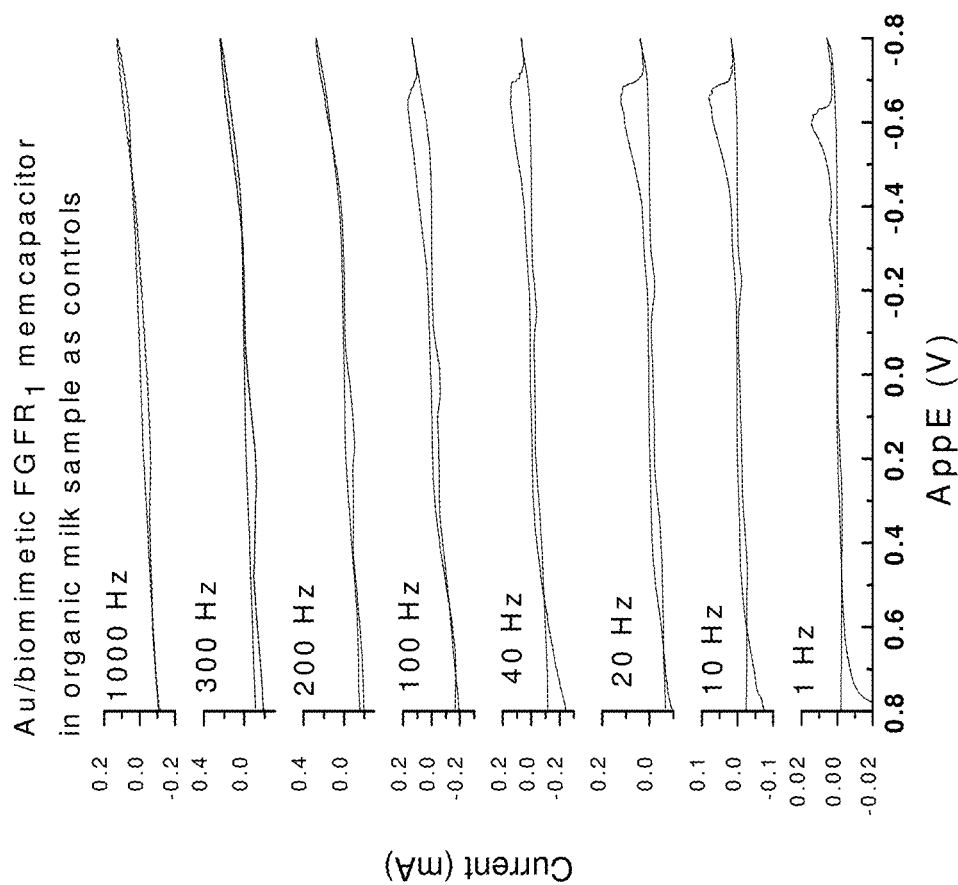
FIG. 4A illustrates the frequency affect on the hysteresis of the i-V curves of the FGFR-1 sensor in pH 7.0 PBS over scan rate from 1 Hz to 1 KHz without LPS.
Figure 4B:
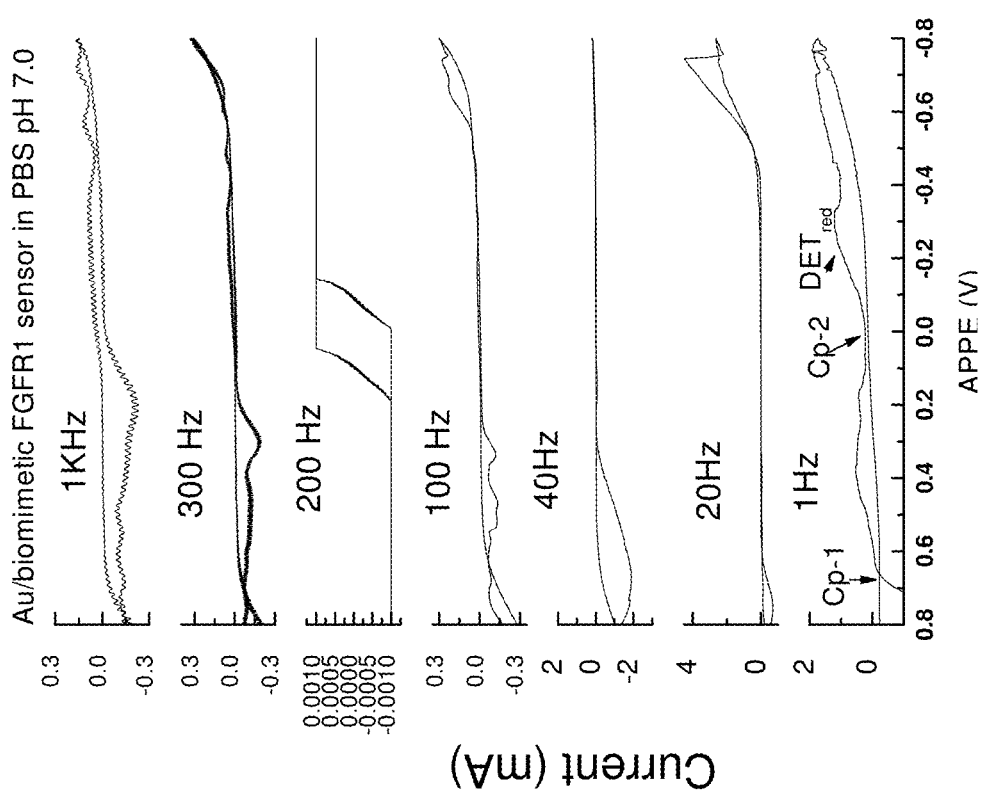
FIG. 4B depicts the CV profiles organic milk controls.
Figure 4D:
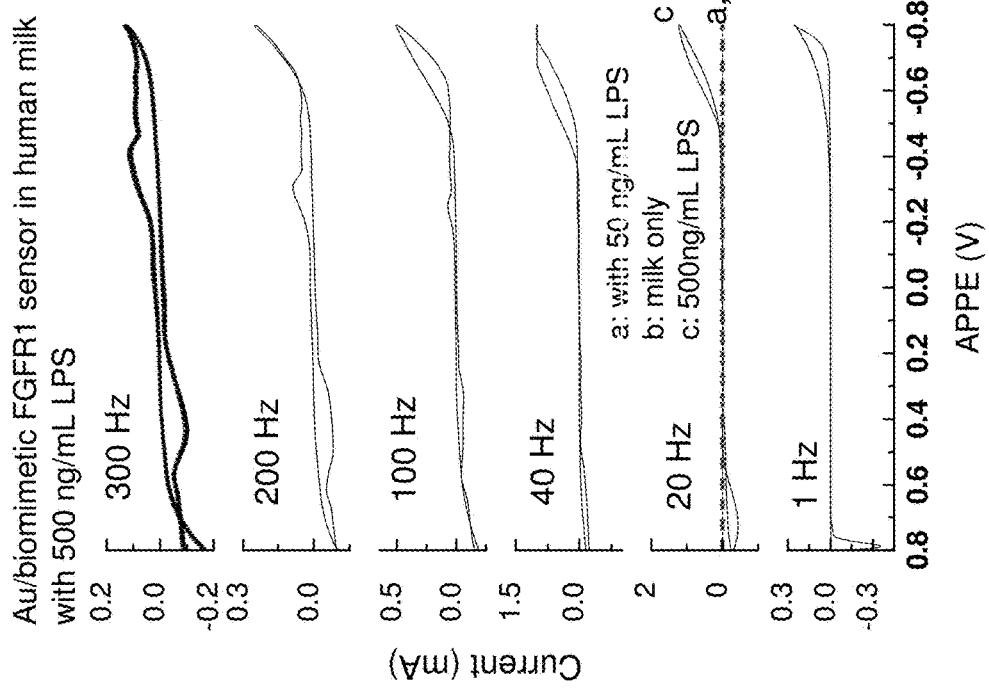
FIG. 4D depicts the CV profiles in 500 ng/mL LPS in human milk.
Figure 4C:
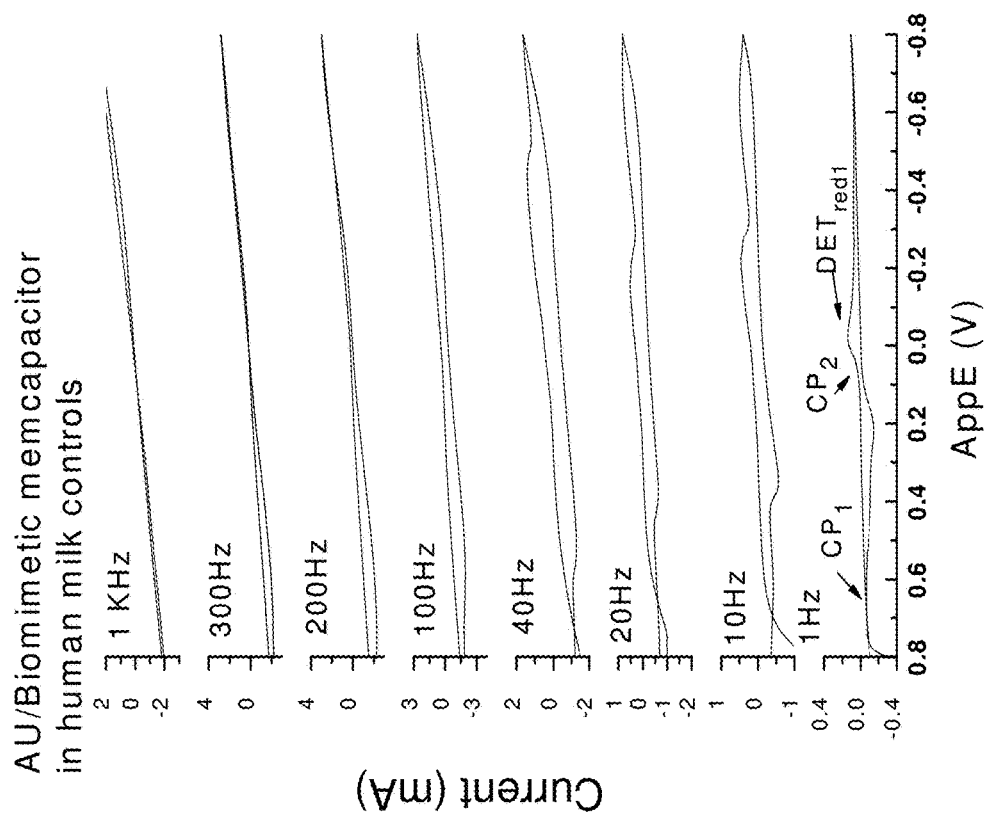
FIG. 4C depicts the CV profiles of human milk controls.

FIG. 4A's i-V hysteresis curves were demonstrated with a switch point at the origin (0, 0) at almost all frequencies, except at kHz high frequency in the control medium PBS. When these perfect hysteresis behavior peaks occurred, especially at SWS frequency with a sensitive Direct Electron-Transfer (DET), and the switch point originates at origin, it indicates a healthy "newborn single neuron" exists before "feeding" it milk samples. Nonlinear frequency influence on current intensity is a characteristic of the memristor as reported in literature [9-12, 37-40]. FIG. 4B shows the controls in organic milk samples over 1 Hz to 1 kHz. The significant difference observed between the organic milk control, the PBS control, and the human milk control at SWS is that the organic milk did not have a butterfly type $DET_{red}$ peak near −0.1 to −0.2 V, where as PBS and human milk had this peak and cross-points near the origin. Rather, the organic milk control had a strange $DET_{red}$ peak at −0.595 V, and the control missed the cross-point near zero V. Further investigation is needed to determine what substances caused the unknown DET peak to occur. FIG. 4C is the human milk controls with well-defined sensory DET butterfly peaks crossed near the origin at SWS. FIG. 4D depicts that in human milk, 500 ng/mL LPS reduced the signal intensity at the SWS significantly. The LPS eliminated the original sensitive DET peaks, and that means the LPS first makes the neuron lose its sense of danger in the presence of toxins; this phenomenon matched our prior observations in the work of β-amyloidal (Aβ) that caused Alzheimer's sensory loss at SWS [9-12, 30, LPS, PSI]. In the worst case, the cow milk with LPS impaired heavily the DET sensory ability of our model neuron as compared to that in human milk, as shown in FIG. 4E.

Example 6—Quantitation of LPS Using the CA Method

The method of use the organic nanobiomimetic memristive/memcapacitive sensing apparatus, further includes procedures of (a) obtaining a sample immersed in a media which can be detected; (b) contacting the sample with the device, the device has SAM membrane mimics the both FGFR1 receptor and CHAT function groups, further due to the presence of embedded o-NPA, the SAM formed mitochondria-like double membrane promoting electron-relay (E-R) and also strengthened structural toroidal array formation; (c) applied a fixed voltage cross the MEA working electrode (as an anode electrode) and a bare gold electrode (as a cathode electrode), the biological media containing either LPS or AcCoA analyte, a changing current occurred due to the E-R amplification of the signal, herein the signal is recorded, which has a correlation to the analyte concentration; (d) wherein the analyte can be detected and quantified by input the sample's current data against the calibration curves to obtain the analyte concentration after subtraction of the background. Quantitation of LPS was conducted with two methods. The first was a Chronoamperometric (CA) method under two steps of fixed potential: −50 mV and −400 mV with each step duration of 100 ms, and the data rate is 20 kHz at room temperature under the conditions of antibody-free, radioactive tracer-free and reagent-free in certified organic milk for infants with seven LPS challenge levels from 5.0 pg/mL to 500 ng/mL against controls, each sample run triplicates.

Figure 6:
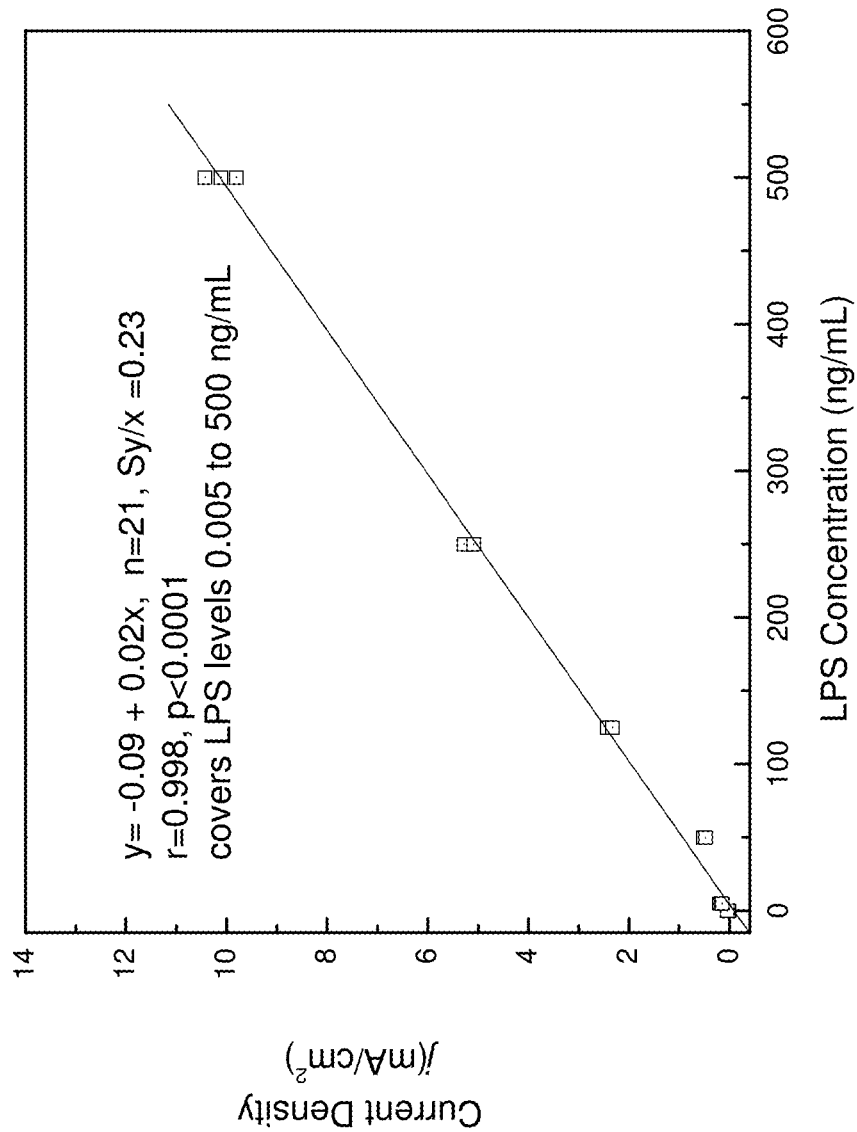
FIG. 6 depicts the calibration plot curve of current density vs. LPS concentrations in organic milks samples using the CA method.

The CA Method. The CA curve profiles were plotted using the biomimetic sensor in the presence of seven LPS concentration levels from 0, 5.0 pg/mL, 50.0 pg/mL, 5.0 ng/mL, 50 ng/mL, 125 ng/mL, and 250 ng/mL to 500 ng/mL against the control in organic milk samples as shown in FIG. 5A. FIG. 5B depicts the lower level LPS's response curves, showing more clearly the significant increase in signals at 5 pg/mL LPS over the control. The CA method for LPS produced a calibration curve with the regression equation $y=-0.09+0.02x$, $n=21$, $S_{y/x}=0.23$, $r=0.998$ with $p<0.0001$ covering the linear range from 5 pg/mL to 500 ng/mL in organic milk samples as shown in FIG. 6. The DOL result is 0.1 pg/mL per one $cm^2$ sensor in organic milk, i.e., by the CA method we are able to detect $5.0 \times 10^{-4}$ EU E. coli in 1 mL sample in 1 $cm^2$ sensor. Using this 0.031 $cm^2$ sensor, we are able to detect E. coli cells in the range of 0.2-5 cell assuming 5 EU contains 2000-50000 E. coli cells' activity [13, LPS, PSI]. The percentage of Pooled Relative Standard Deviation (PRSD %) of the organic milk samples over the entire linear range is 2.0%.

Example 7—Quantitation of LPS Using the Voltage Method

The second quantitation method was the voltage method, i.e., the DSCPO method, and the conditions were the same as described in the section of Assessing Energy Outcomes under Challenges of LPS by using human milk and organic cow milk samples under 4-5 LPS challenges from 50 ng/mL to 1000 ng/mL, respectively at ±10 A against controls at 0.25 and 200 Hz, respectively. Freshly obtained samples were without pretreatment. Human milk cooled by dry ice was delivered to the laboratory, and it was brought to room temperature naturally without any heating before spiking the LPS. All water used was autoclaved and double distilled from Fisher Scientific. LPS was purchased from Sigma, and it was dissolved in autoclaved and filtered PBS pH 7.0 buffers.

The Double Step Chronopotentiometry (DSCPO) method, as the voltage method, was used for assessing energy outcomes of slow-wave-sleeping (SWS) at 0.25 Hz and 200 Hz under the challenge of LPS at concentration ranges from 0, 50, 100, 500, to 1000 ng/mL of 4-5 levels with triplicates at ±10 nA, respectively. Samples were tested at each level without prior sample preparation, such as dilution or heating. The experiments were conducted at room temperature. The milk samples compared were human milk and USDA certified organic cow milk for infants, with and without LPS. Human milk was collected from a normal subject who breastfeeds a 1 month-old newborn (Lee Biosolutions Corp.). An electrochemical workstation was used (Epsilon, BASi, IN) with a software package from BASi. OriginPro 2016 (Origin Lab Corp., MA) was used for all statistical data analysis and figure plotting.

Figures 9A, 9B:
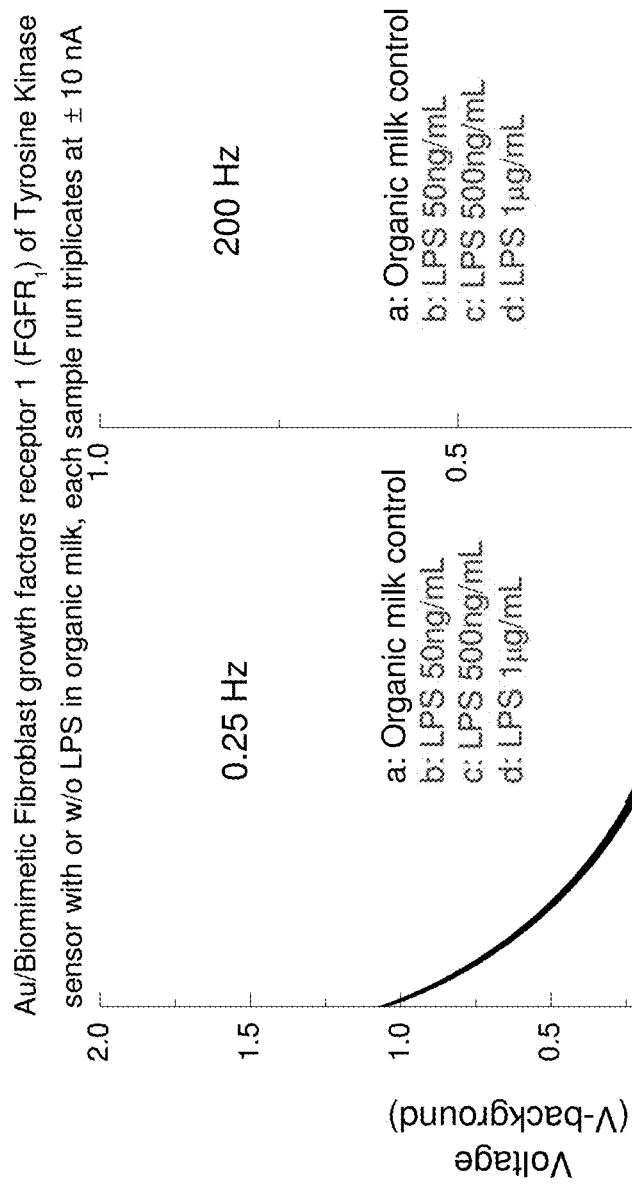
FIG. 9A compares the LPS effects on organic cow milk over 0, 50, 500 to 1000 ng/mL at 0.25 Hz
FIG. 9B depicts the voltage curves of organic mil at 200 Hz, respectively.
Figure 10B:
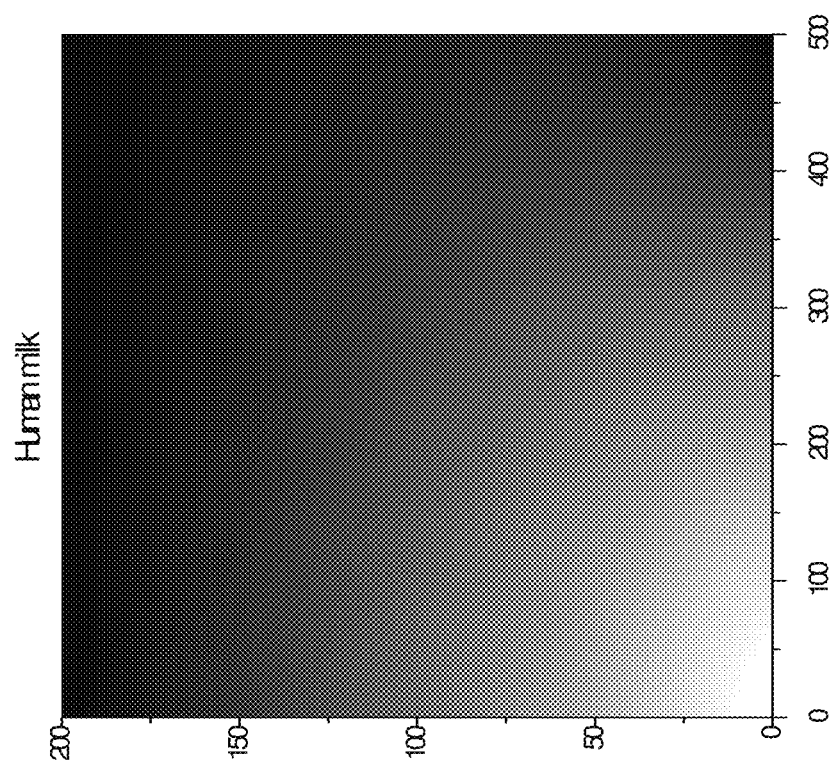
FIG. 10A and FIG. 10B depict the energy density (as Z) contour map and the image, respectively, are shown using human milk. The LPS concentration (as X) and synapse frequency (as Y).
Figure 10A:
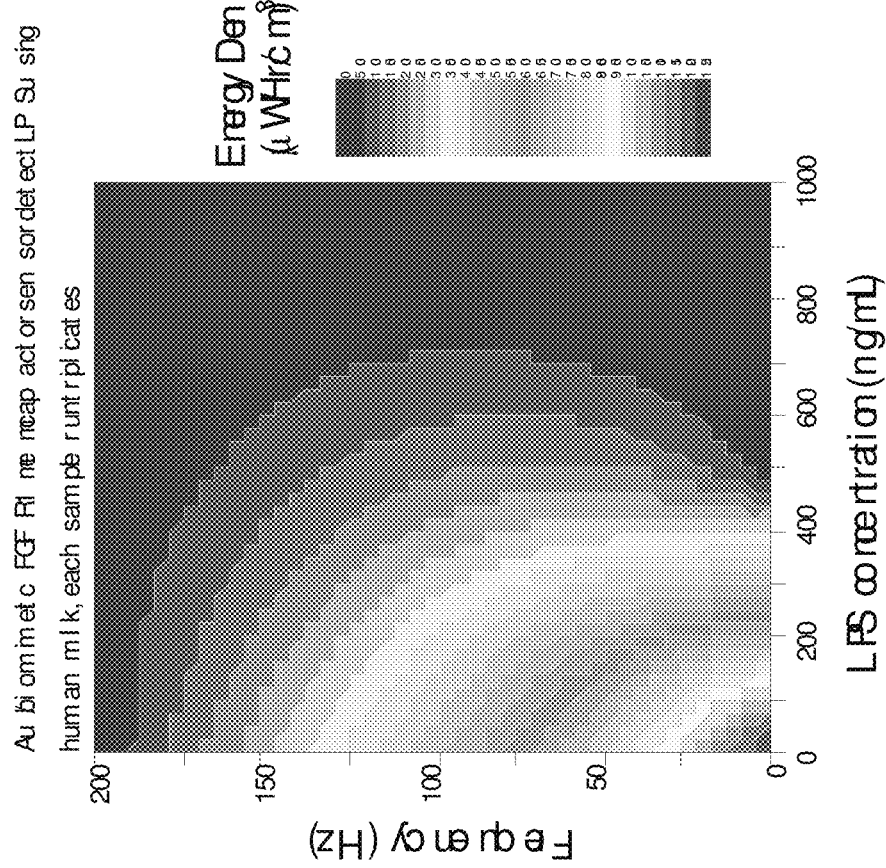
Figure 10C:
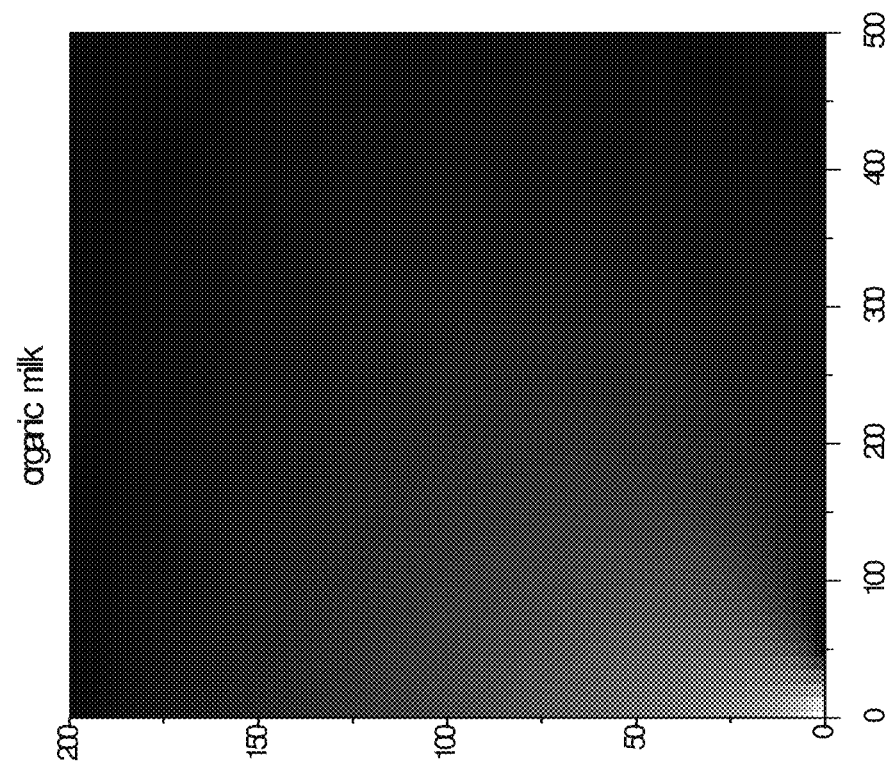
FIG. 10C and FIG. 10D depict the energy density (as Z) contour map and the image, respectively, are shown using organic milk in the presence of the LPS concentration (as X) and synapse frequency (as Y).
Figure 10D:
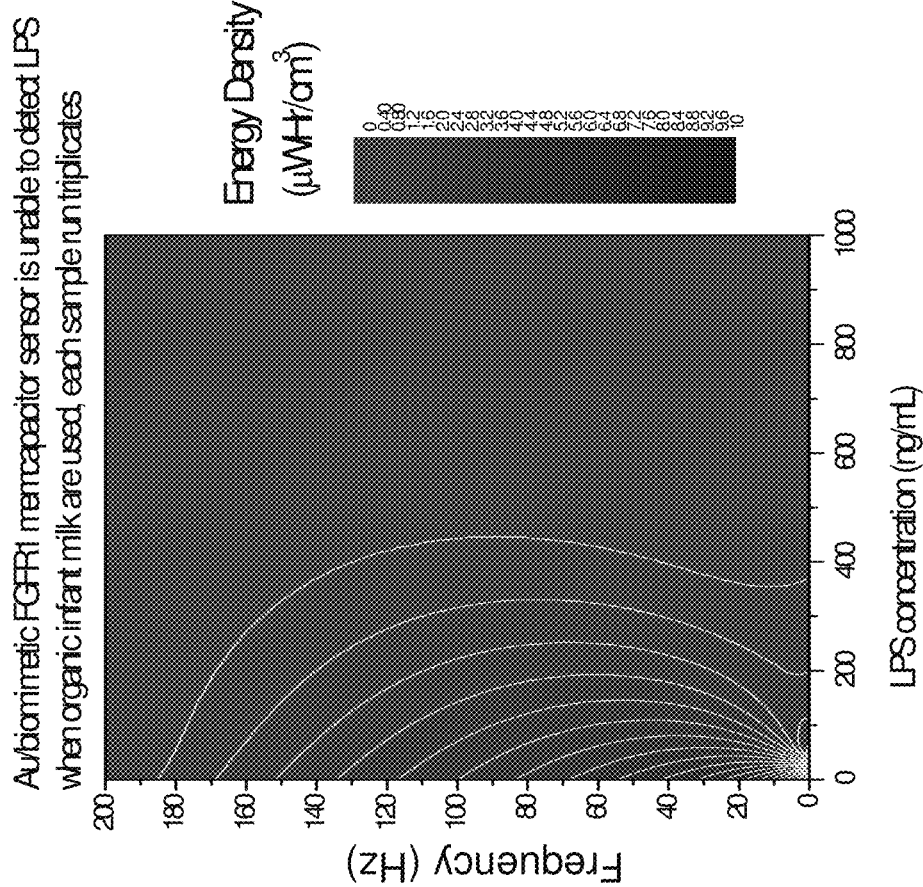

Assessing energy outcomes was conducted by comparing human milk and certified organic milk, both with and without LPS, at 0.25 Hz and 200 Hz, respectively, using the voltage method. FIG. 7A, 7B, 7C depict the synapse pulse control profiles using human milk, and compares samples using PBS media at 0.25, 40, 100, 200 and 250 Hz, respectively, without LPS. Curves overlap between the two media, and indicate human milk had no protein interference with the "single neuronal cell" as far as the neuron's energy output is concerned. FIG. 7D compares the signal intensity when testing human milk in the presence of various LPS concentrations at 0.25 Hz and the results show the signal intensity is inversely proportional to a wide range of LPS concentrations from 50 ng/mL to 1000 ng/mL at 0.25 Hz. At 50 to 100 ng/mL, the biphasic pulse shape integrity is maintained; however the insert curves show that at 500 and 1000 ng/mL, the biphasic pulses are destroyed, and the cell net voltage intensity is close to zero. FIG. 7E demonstrates a similar trend at 200 Hz, that the cell net voltage gets close to zero, at a higher concentration at 200 Hz, but at 50 ng/mL, the signal increases more than 30% compared with that at zero LPS. This is a bad effect, a negative outcome of wasted energy. FIG. 8A depicts the quantitative calibration plot of LPS in human milk at 0.25 Hz and FIG. 8B depicts the plot at 200 Hz compared with LPS in organic milk at 0.25 Hz (FIG. 8C) and 200 Hz in FIG. 8D. FIG. 9A compares the LPS effects on organic cow milk over 0, 50, 500 to 1000 ng/mL at 0.25 Hz and FIG. 9B depicts the voltage curves of organic mil at 200 Hz, respectively.

The use of Double Step Chronopotential (DSCPO) method by the organic nanobiomimetic memristive/memcapacitive sensing apparatus further includes procedures of (a) obtaining a sample immersed in a media which can be detected; (b) contacting the sample with the device, the device has SAM membrane mimics the FGFR1 receptor, further due to the presence of embedded o-NPA, the SAM formed mitochondria-like double membrane promoting electron-relay (E-R); (c) applied a fixed pulse current cross the MEA working electrode (as an anode electrode) and a bare gold electrode (as a cathode electrode); (d) setting up appropriate pulse stepping time in order to measure the potential; (e) measuring the sample containing LPS analyte, a changing electrochemical potential occurred due to the E-R amplification of the signal compared with the media control, herein the potential is recorded, which the intensity has a correlation to the analyte concentration, wherein the LPS analyte can be detected and quantified by using the calibration curves. Because LPS is a gram-negative antigen protein existing on the membrane surface of a living $E$ $coli$ cell in the $10^{-17}$ g range, herein an endotoxin single $E$ $coli$ cell can be detected and quantified. FIG. 8A illustrates the linear calibration curve at 0.25 Hz of volumetric energy density vs. LPS concentration range from 50 to 500 ng/mL using human milk, and it produced a linear regression equation Y=125−0.25X, r=0.9993 (n=12), P<0.0001, Sy/x=2.0. The Detection of Limits (DOL) is 0.3 ng/mL, i.e., in a 40μL sample; it detects 12 pg LPS using a 1 cm$^3$ sensor, our sensor is 3.11×10$^{-7}$ cm$^3$. Herein the DOL in our sensor is 3.73×10$^{-18}$ g for LPS means we are able to detect a single $E$. $coli$ bacterium because an antigen is in $10^{-17}$ g range. At 0.25 Hz, the energy density ranges between 123.2 and 0.11 μWHr/cm$^3$ using human milk specimens with an imprecision value 3.0% compared the energy range of 9.8 to −0.042 μWHr/cm$^3$ for organic milk. FIG. 8B shows the nonlinear curve for LPS at 200 Hz using human milk. In contrast, FIGS. 8C and 8D show no sensitivity towards LPS over the same concentration range using organic milk. Human milk offers more than 12.5-fold high energy than organic milk and 100-fold sensitivity for LPS than organic milk.

Example 8—A Contour Mapping Method for Evaluation of Human Milk Immunological Advantage Under the LPS Challenge The data obtained from the quantitation using the voltage method was used for evaluation of human milk immunological advantage under LPS challenges compared with that of the organic cow milk samples in 3D mapping method. The energy density results were put into the "y" column, the spiked LPS concentration over 0.0 to 1000 ng/mL was put into the "x" column, and the frequency was at the "z" column having two levels of 0.25 to 200 Hz. After converting the three data columns into a random XYZ correlation matrix, one can plot the contour maps and analyze the spatiotemporal formation of the pHFO, if it exists among human milk or organic milk samples. The real-time data obtained from the DSCPO method was converted to volumetric energy density, $E=C_s \cdot (\Delta V)^2/(2 \times 3600)$, where $C_s$ is the specific volumetric capacitance, $C_s=[-i \cdot \Delta t / \Delta V]/L$, $C_s$ is in F/cm$^3$ [33-34], $\Delta t$ is the time in second, $\Delta V$ is the voltage in V, i is the current in Amps, and L is the volume in cm$^3$.

The energy density contour maps associated with the images are presented in FIG. 10 with energy density as Z, LPS concentration as X, and discharge pulse frequency as Y. FIGS. 10 A and 10B depict the contour map of energy density vs. LPS concentration in the frequency change using the human milk samples and FIGS. 10C and 10D depict the contour map of energy density vs. LPS concentration in the frequency change using the organic milk samples. It is obvious that human milk produced tremendous higher energy (showing as the light in the image) with an intensity more than 10-fold higher, especially at SWS even in the presence of LPS.

Example 9—Evaluation of Immunological Advantage Under LPS Challenges

Figure 11A:
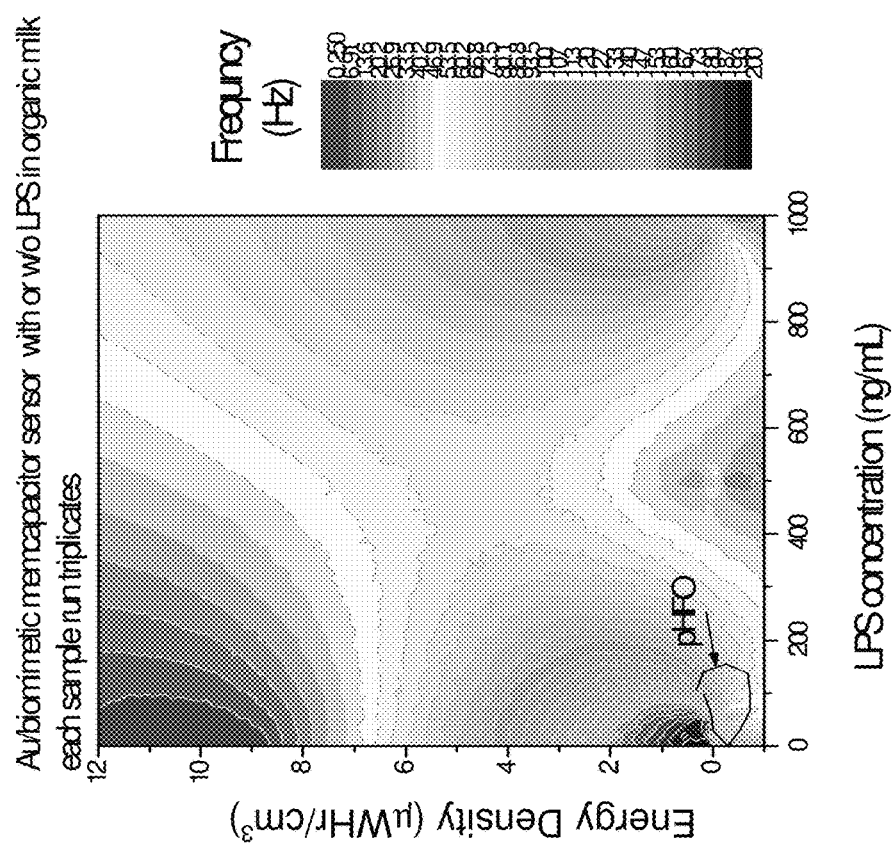
FIG. 11A depicts the 3D energy distribution map vs. frequency and LPS concentrations in human milk.
Figure 11B:
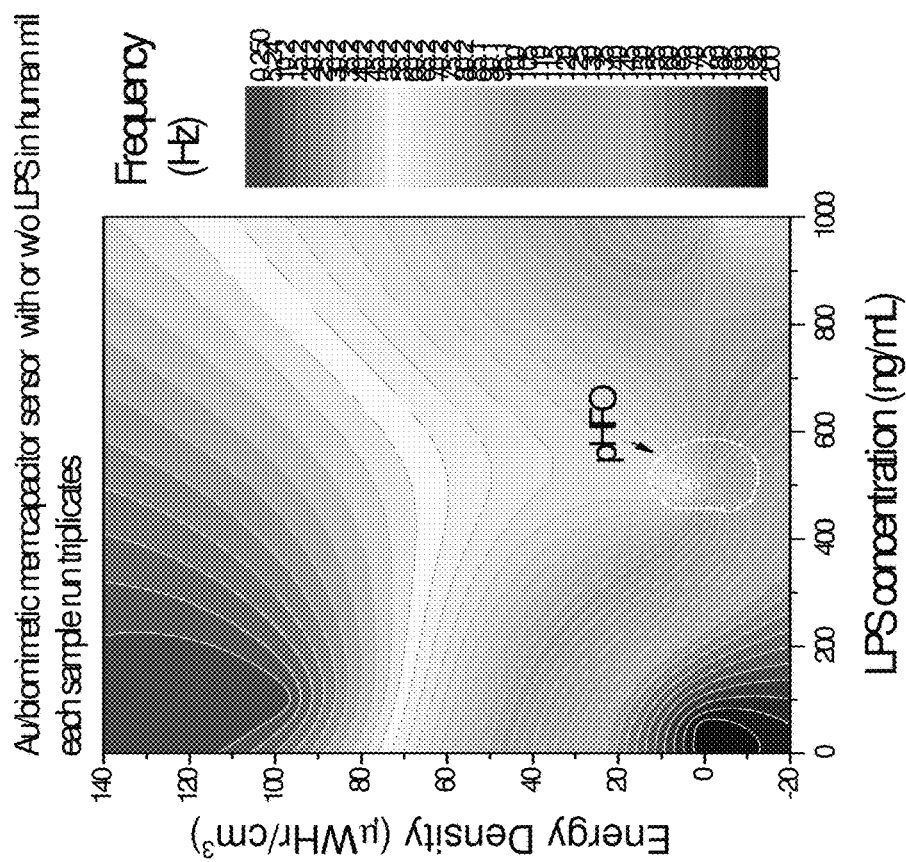
FIG. 11B depicts the 3D energy distribution map vs. frequency and LPS concentrations in organic milk.

The comparisons of the immunological advantage under LPS challenges were evaluated through the study of the formation of the pHFO using a 3D energy density map method. The energy density results were put into the "y" column, the spiked LPS concentration over 0.0 to 1000 ng/mL put into the "x" column and the frequency was into "z" column having two levels of 0.25 to 200 Hz. After converting the three data columns into a random XYZ correlation matrix, one can plot the contour maps and analyze the spatiotemporal formation of the pHFO if a pHFO exists among human milk or organic milk samples. FIG. 11A depicts a 3D contour map of the relationship between energy density, LPS concentration and frequency using human milk. As we can see, at SWS, human milk held the highest neural synapse energy for with or without the presence of LPS challenge over the range from 0.0 ng/mL LPS to less than 200 ng/mL, until the LPS reaches 500 ng/mL, the energy gradually reduced to zero, in other words, human milk samples have an order of magnitude higher energy density at LPS=0 vs. organic milk at SWS and 200 Hz, respectively as shown in FIG. 11 A compared with FIG. 11B. At 0.25 Hz, 50 ng/mL LPS caused 100% energy reduce in organic milk vs. human milk only 6.25% reduced. The rate of LPS reducing synapse energy is 10-times faster in organic milk samples than in human milk samples. It is estimated from the map at LPS 5 EU/ng, human milk maintained 96.6% original energy strength vs. organic milk only 49% strength at 0.25 Hz.

Figure 12:
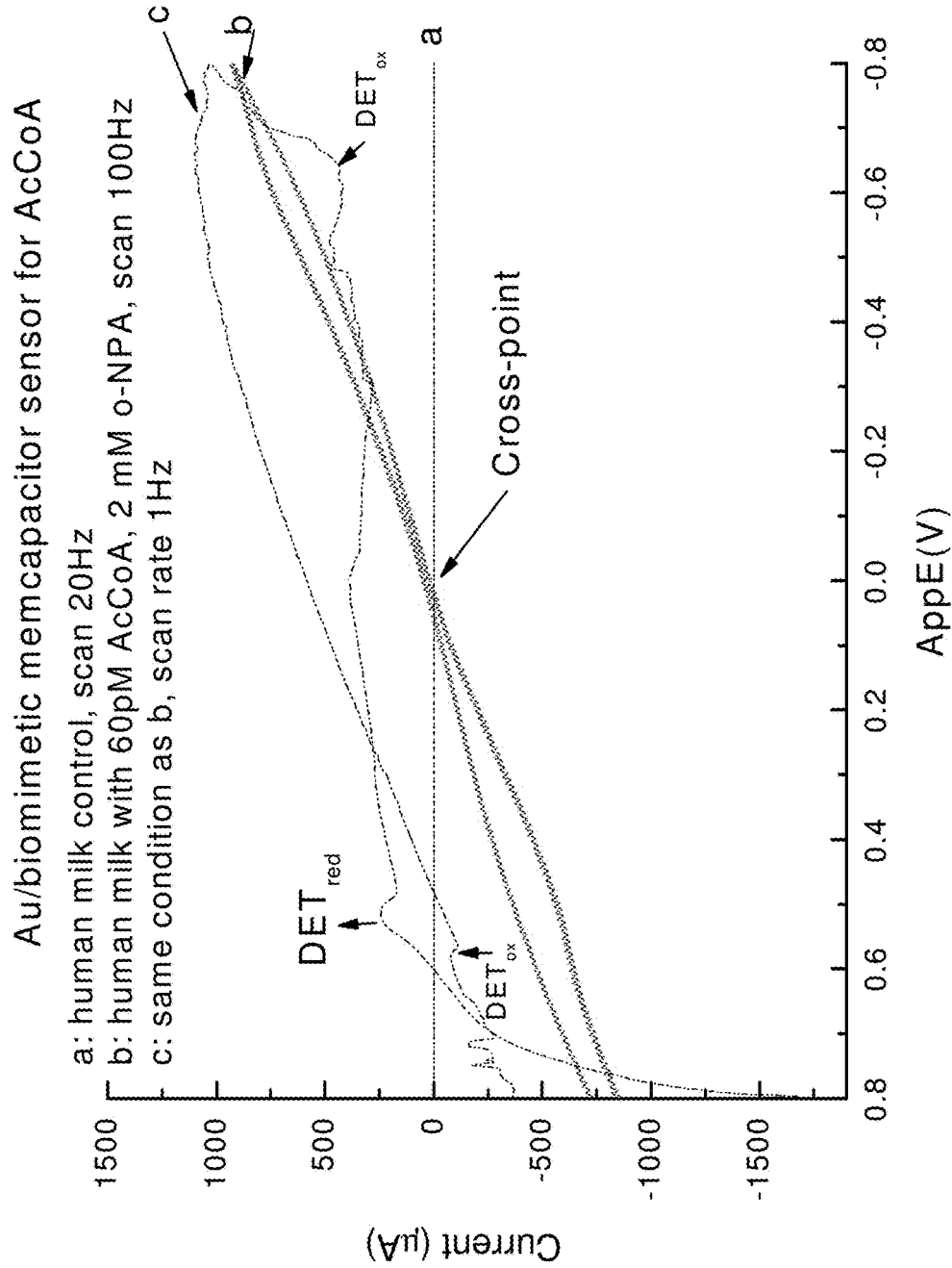
FIG. 12 depicts the CV profiles in human milk with and w/o AcCoA.
Figure 13:
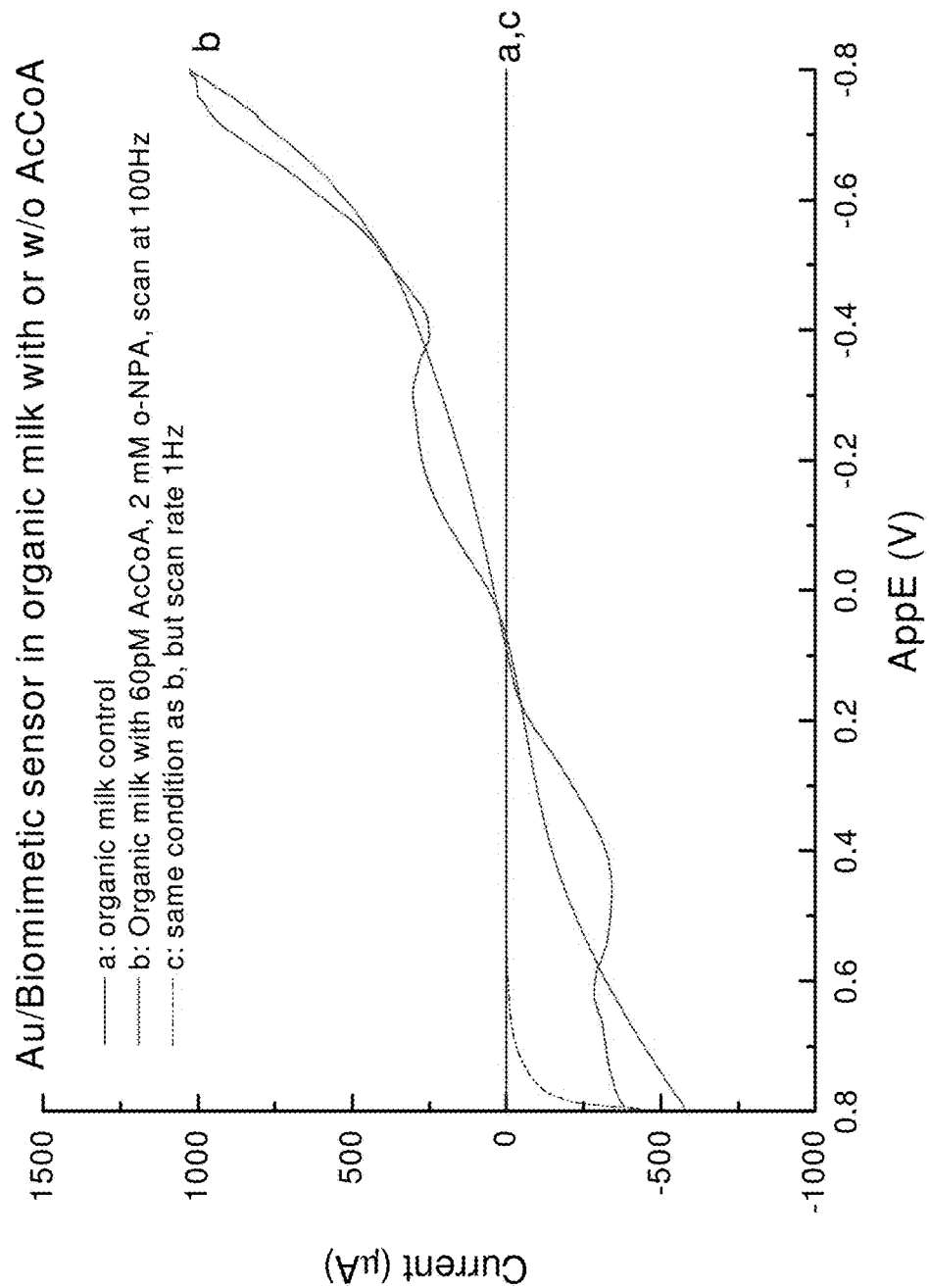
FIG. 13 illustrates the CV curves in organic milk with and w/o AcCoA.

Example 10—Assessing the Neuronal Network Sensory by DET and the Hysteresis Switch Point A "neuron" memristor's performance in i-V curves using fresh human milk or organic milk with or without 60 pM AcCoA as shown in FIG. 12 and FIG. 13. The sensor responded to human milk and organic cow milk differently. For example, at 1 Hz, the sensor has more DET peak and hysteresis switch points with human milk compared to organic milk, which has none, regardless of whether the samples are tested with or without AcCoA. These figures revealed human milk provides the single neuron a critical sensory function at the memory consolidation stage of brain development, and safe guards the reversible membrane potential in place, and ensures the normal function of direct electron-relay. The possible source or cause may be the contribution of the good bacteria as compared to the cow milk, which has none [www.en.wikipedia.org], because pasteurization of cow milk destroys both good and bad bacteria [www.en.wikipedia.org]. Another source which may contribute to the brain development may be the unique proteins such as A2 β-casein, which is plentiful in human milk, and lacking in cow milk [S. Ho et al., *European J. of Clinical Nutrition* 68(9), 994-1000, 2014]. FIG. 13 shows there are no DET peak and no cross-point occurrence at 1 Hz with organic milk, and that indicates the cow milk offers a disadvantage for infant development compared with human milk. In contrast, at 100 Hz, the cross-points and DET peaks showed up in the i-V curve when spiked with AcCoA, and that may be the key reason causing energy drainage as evidenced in following sections. However, a dosage of AcCoA at 60 pM does do damage to the neuron even when using human milk, as evidenced by the moving away of the cross-point from the origin, and the energy was reduced as shown in the following section.

Example 11—Quantitation of AcCoA by the CA Method

Figure 14:
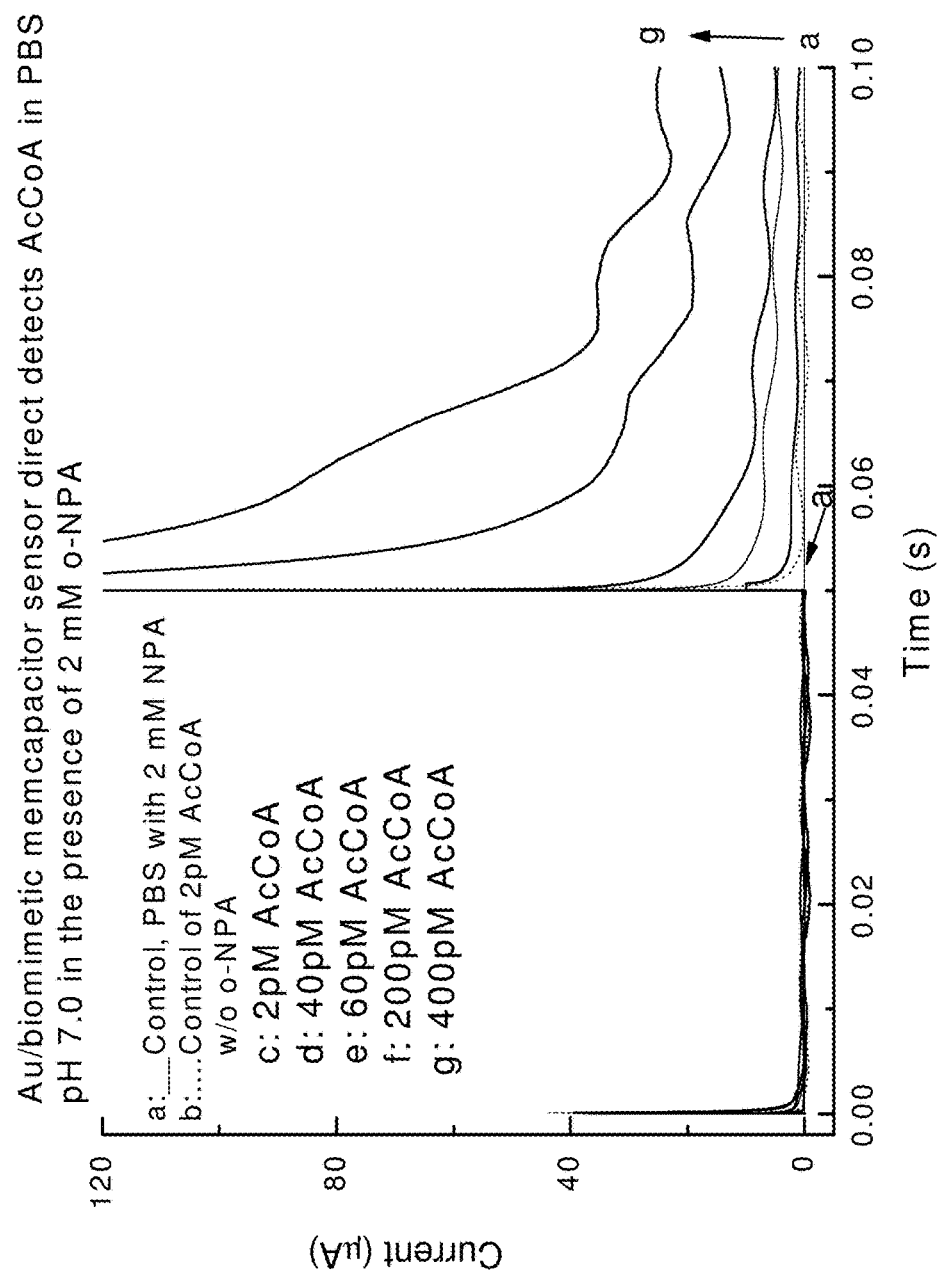
FIG. 14 illustrates the CA curve profiles in PBS pH 7.0 in the presence of 2 mM o-NPA.

The CA method procedures are cited in paragraphs [00048]. The data were acquired at room temperature under two-step fixed potentials in 6 concentration levels covering AcCoA final concentrations ranging from $2.0\times10^{-12}$M to $4.0\times10^{-10}$M, with triplicates in pH 7.0 PBS in the presence of 2 mM o-NPA against 2 controls, one with 2 mM o-NPA, and another control without o-NPA. Accuracy was accessed by organic milk specimen samples with 60 pM spiked AcCoA, run triplicates; obtain the signal and then using the sample signal divided by the data obtained from the calibration curve to obtain the percentage of recovery. FIG. 14 illustrates CA curve profiles of AcCoA over the linear range of $2.0\times10^{-12}$M to $4.0\times10^{-10}$M in the presence of 2 mM o-NPA. The role of o-NPA is for enhancing of the hydrophobicity [16, 18-19], and it has no signal interference with AcCoA as shown in the control. The profiles show the signal intensity is in direct proportion to the increase of the AcCoA concentration. FIG. 15 illustrates the calibration curve with a linear regression equation Y=2.1+57X, r=0.994 (n=15), P<0.0001, Sy/x=0.95. The value of Detection of Limits (DOL) is $1.2\times10^{-12}$ M/cm$^2$. Because this sensor is only 0.031 cm$^2$, hence, its DOL is 37 fM in PBS. The measurements can be extended to an exponential nonlinear model from 2 pM to 0.30 μM with y=A1*exp(-x/t1)+A2*exp(-x/t2)+y0, y0=1225.5, A1=-916, A2=-372, t1=0.964, t2=64.5, Chi^2/DoF=17255.7, r=0.98, n=27, 9 levels. Curve fit was not shown. The recovery value using milk at 60 pM AcCoA is 103±2%. The imprecision of milk samples in 60 pM AcCOA is 1.75% (n=12). FIG. 16 depicts the extended plot of current vs. AcCoA concentrations from 2.0 pM up to 0.3 μM.

Example 12—Quantitation of AcCoA by the DSCPO Method

Quantitation of AcCoA and assessing the energy outcomes were conducted by comparing human milk and the USDA certified organic cow milk for infants, both with and without 60 pM AcCoA, at 0.25 Hz and 250 Hz, respectively, using the DSCPO method. The use of the method was disclosed in [00048]. FIG. 17A depicts the 60 pM AcCoA reduced the synapse voltage discharge by 94% at 0.25 Hz in human milk compared without AcCoA. AcCoA reduced more energy outcome at SWS as compared at 250 Hz, as shown in FIG. 17B. Also shown, the good bacteria in human milk boosted the net energy of five-fold, 1.04 nWHr/cm$^2$ compared 0.19 nWhr/cm$^2$ of organic milk without AcCoA at 0.25 Hz; and 25.3 pWHr/cm$^2$ with human milk compared with 37 pWHr/cm$^2$ of organic milk in the presence of 60 pM AcCoA at 0.25 Hz as shown in FIG. 18A and FIG. 18B. From these results, human milk offers great benefits than organic cow milk for the development of neuronal cells at all frequencies studied regardless of whether it contains AcCoA. The biphasic synapse curves with the highest intensity at SWS over other frequencies are the characteristics of the normal human brain function, and it originating energy for memory consolidation demonstrated using the nanobiomimetic memristor/memcapacitor device using human milk. Using the same device has a destroyed biphasic synapse pattern with so low energy outcome using organic milk as shown in FIG. 18A at 0.25 Hz and FIG. 18B in 250 Hz, with and without AcCoA, indicates there is an urgent need to enrich the probiotic in the cow milk for children. All evidences presented here clearly and convincingly shows that human milk increases the energy available to output to the neuronal cell for further brain developing, and which supports a strong recommendation by the authors to women to seriously consider the advantages of breast-feeding to infant brain development and health Example 13—Potential Application in Superconducting According to FIG. 4A, the device has potential application in superconducting device at zero-bias with 200 Hz scan rate in PBS solution with ±1 μA peak superconducting current. FIG. 5A, FIG. 5B and FIG. 14 demonstrated the sine curvatures with oscillation in both situations for with and without analyte, either LPS or AcCoA indicated the toroidal arrays configuration induced the amplified supercurrent at a finite applied $V_{dc}$ potential (-600 mV) for LPS and (-200 mV) for AcCoA, respectively.

What is claimed is:
1. A direct single endotoxin cell detecting device comprising:
   a. an electrode comprising a substrate of gold; and
   b. a self-assembling membrane (SAM) comprising a polymer matrix comprised of an electrically conductive copolymer; wherein the copolymer is further comprised of:
      i. one or more β-cyclodextrin copolymers having at least one or more acetyl groups;
      ii. one or more polyethylene glycol polymers; and
      iii. one or more poly(4-vinylpyridine) polymers;
   wherein at least some of the one or more β-cyclodextrin copolymers forming the SAM have a mitochondria-like surface structure comprising an array of nano islands; and
   wherein the nano islands are vertically oriented and affixed on the substrate; and
   wherein an embedded organic hydrophobic material forms an electron-relay network with the nano islands that mimics active sites during electron-relaying of Fibroblast Growth Factor Receptor 1 (FGFR1) or choline acetyltransferase (CHAT).

2. According to claim 1, wherein function groups of the SAM of the device interacts with the organic hydrophobic material o-nitrophenyl acetate (o-NPA) formed an electron-relay network with TCD, PEG PVP, and β-CD co-polymer enabled to mimic Acetyl CoA (AcCoA)'s binding sites C563, C550, Y552, H324, and S540 of CHAT.

3. According to claim 2, wherein the device has a toroidal array dual sensing function of single molecule *E. coli* and Acetyl CoA.

4. According to claim 3, wherein an organic nanobiomimetic memristive/memcapacitive sensing apparatus have a nanometer air gap serving as a dielectric insulator between electron-relay circuits.

5. According to claim 4, wherein the device directly measured and monitored endotoxin and its energy outcomes is Lipopolysaccharide (LPS) from *E. coli* in biological fluid under antibody-free, tracers-free, and reagent-free conditions using a double step chronopotentiometry (DSCPO) method.

* * * * *